US009439941B2

(12) United States Patent
Ellis-Behnke et al.

(10) Patent No.: US 9,439,941 B2
(45) Date of Patent: Sep. 13, 2016

(54) NANO CANCER BARRIER DEVICE (NCBD) TO IMMOBILIZE AND INHIBIT THE DIVISION OF METASTIC CANCER STEM CELLS

(75) Inventors: Rutledge Ellis-Behnke, Hong Kong (CN); Patrick Ming Tat Ling, Queensland (AU)

(73) Assignee: The University of Hong Kong, Hong Kong (CN)

( * ) Notice: Subject to any disclaimer, the term of this patent is extended or adjusted under 35 U.S.C. 154(b) by 693 days.

(21) Appl. No.: 12/967,708

(22) Filed: Dec. 14, 2010

(65) Prior Publication Data

US 2011/0144023 A1 Jun. 16, 2011

Related U.S. Application Data

(60) Provisional application No. 61/286,166, filed on Dec. 14, 2009.

(51) Int. Cl.
| | |
|---|---|
| A61K 38/10 | (2006.01) |
| C12N 5/00 | (2006.01) |
| A61P 35/00 | (2006.01) |
| A61P 7/04 | (2006.01) |
| C12Q 1/02 | (2006.01) |
| A61K 38/08 | (2006.01) |
| B82Y 5/00 | (2011.01) |

(52) U.S. Cl.
CPC ............... *A61K 38/10* (2013.01); *A61K 38/08* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 4,098,728 | A | 7/1978 | Rosenblatt |
| 4,211,227 | A | 7/1980 | Anderson |
| 4,272,398 | A | 6/1981 | Jaffe |
| 4,636,208 | A | 1/1987 | Rath |
| 4,861,627 | A | 8/1989 | Mathiowitz |
| 5,126,141 | A | 6/1992 | Henry |
| 5,180,375 | A | 1/1993 | Feibus |
| 5,192,302 | A | 3/1993 | Kensey |
| 5,222,974 | A | 6/1993 | Kensey |
| 5,645,565 | A | 7/1997 | Rudd |
| 5,670,483 | A | 9/1997 | Zhang |
| 5,762,846 | A | 6/1998 | Blankenbeckler |
| 5,955,343 | A | 9/1999 | Holmes |
| 6,333,194 | B1 | 12/2001 | Levy |
| 6,368,877 | B1 | 4/2002 | Zhang |
| 6,548,630 | B1 | 4/2003 | Zhang |
| 6,663,655 | B2 | 12/2003 | Ginn |
| 6,711,879 | B2 | 3/2004 | Korteweg |
| 6,800,116 | B2 | 10/2004 | Stevens |
| 6,800,481 | B1 | 10/2004 | Holmes |
| 6,844,324 | B1 | 1/2005 | Zhang |
| 6,953,656 | B2 | 10/2005 | Jacobson |
| 6,953,659 | B2 | 10/2005 | Jacobson |
| 7,098,028 | B2 | 8/2006 | Zhang |
| 7,179,784 | B2 | 2/2007 | Zhang |
| 7,449,180 | B2 | 11/2008 | Kisiday |
| 7,534,448 | B2 * | 5/2009 | Saltzman et al. ............. 424/417 |
| 7,700,721 | B2 | 4/2010 | Boden |
| 7,704,740 | B2 | 4/2010 | Schindler |
| 7,846,891 | B2 | 12/2010 | Ellis-Behnke |
| 8,021,570 | B2 | 9/2011 | Gellman |
| 8,022,178 | B2 | 9/2011 | Horii |
| 8,039,258 | B2 | 10/2011 | Harris |
| 8,512,728 | B2 | 8/2013 | Ladet |
| 8,568,637 | B2 | 10/2013 | Gazit |
| 2001/0024784 | A1 | 9/2001 | Wagner |
| 2002/0072074 | A1 | 6/2002 | Zhang |
| 2002/0160471 | A1 | 10/2002 | Kisiday |
| 2003/0008011 | A1 | 1/2003 | Mershon |
| 2003/0166846 | A1 | 9/2003 | Rothstein |
| 2003/0176335 | A1 | 9/2003 | Zhang |
| 2004/0011201 | A1 | 1/2004 | Stevens |
| 2004/0023414 | A1 | 2/2004 | Zhang |
| 2004/0087013 | A1 | 5/2004 | Holmes |
| 2004/0204561 | A1 | 10/2004 | Ellison |
| 2004/0242469 | A1 | 12/2004 | Lee et al. |
| 2005/0107289 | A1 | 5/2005 | Ghadiri |
| 2005/0181973 | A1 | 8/2005 | Genove |

(Continued)

FOREIGN PATENT DOCUMENTS

| | | |
|---|---|---|
| GB | 1006606 | 10/1965 |
| JP | 2005074079 | 3/2005 |

(Continued)

OTHER PUBLICATIONS

Collins et al. Cancer Res 2005; 65:23, 10946-10951.*
Zhange et al. Senimars in Cancer Biology 15(2005) 413-420.*
Evolution and Prostate Cancer, vol. V, Winter 2000, http://urology.jhu.edu/newsletter/prostate_cancer511.php. Accessed to the website on Oct. 31, 2013.*
Sigma-Aldrich amino acids reference chart p. 3, Properties of Common Amino Acids 3 pages. Jul. 23, 2014.*
Cadroy et al. (J Clin. Invest vol. 84, Sep. 1989, pp. 939-944).*
"Designing Custom Peptides," from SIGMA Genosys, pp. 1-2. Accessed Dec. 16, 2004.

(Continued)

*Primary Examiner* — Amber D Steele
*Assistant Examiner* — Schuyler Milton
(74) *Attorney, Agent, or Firm* — Pabst Patent Group LLP

(57) ABSTRACT

The present invention provides methods, compositions, and kits wherein nanomaterials are used for inhibiting cancer stem cell division, colony formation, spheroid formation and self-renewal. The present invention also provides methods, compositions, and kits wherein nanomaterials are used for treating cancer, coating tumors, and inhibiting metastasis. The present invention also provides methods, compositions, and kits wherein nanomaterials are used for inducing cells to go into stasis. The present invention further provides methods for isolating tumors, inhibiting bleeding, and marking margins of tumors and organs during surgery with a nanomaterial.

20 Claims, 1 Drawing Sheet

(56) References Cited

U.S. PATENT DOCUMENTS

| | | | |
|---|---|---|---|
| 2005/0214257 | A1* | 9/2005 | Zhao et al. ............. 424/93.2 |
| 2005/0287185 | A1 | 12/2005 | Wong |
| 2005/0287186 | A1 | 12/2005 | Ellis-Behnke |
| 2006/0019309 | A1 | 1/2006 | Zhang |
| 2006/0025524 | A1 | 2/2006 | Schneider |
| 2006/0084607 | A1 | 4/2006 | Spirio |
| 2006/0088510 | A1 | 4/2006 | Lee |
| 2006/0148703 | A1 | 7/2006 | Lee |
| 2006/0199778 | A1 | 9/2006 | Ellis-Behnke |
| 2006/0211615 | A1 | 9/2006 | Zhang |
| 2007/0203062 | A1 | 8/2007 | Ellis-Behnke |
| 2007/0287741 | A1 | 12/2007 | Herzberg |
| 2008/0032934 | A1 | 2/2008 | Ellis-Behnke |
| 2008/0091233 | A1 | 4/2008 | Ellis-Behnke |
| 2008/0274979 | A1 | 11/2008 | Ellis-Behnke |
| 2009/0111734 | A1 | 4/2009 | Ellis-Behnke |
| 2009/0162437 | A1 | 6/2009 | Horii |
| 2012/0010140 | A1 | 1/2012 | Ellis-Behnke |
| 2012/0085262 | A1 | 4/2012 | Klimov |

FOREIGN PATENT DOCUMENTS

| | | |
|---|---|---|
| WO | 9509659 | 4/1995 |
| WO | 9640033 | 12/1996 |
| WO | 9737694 | 10/1997 |
| WO | 9840112 | 9/1998 |
| WO | 9858967 | 12/1998 |
| WO | 9952574 | 10/1999 |
| WO | 02058749 | 8/2002 |
| WO | 02062961 | 8/2002 |
| WO | 02062969 | 8/2002 |
| WO | 03006043 | 1/2003 |
| WO | 03084980 | 10/2003 |
| WO | 03096972 | 11/2003 |
| WO | 2004007532 | 1/2004 |
| WO | 2005014615 | 2/2005 |
| WO | 2005123760 | 12/2005 |
| WO | 2006014570 | 2/2006 |
| WO | 2006036826 | 4/2006 |
| WO | 2006076042 | 7/2006 |
| WO | 2006116524 | 11/2006 |
| WO | 2007142757 | 12/2007 |
| WO | 2008113030 | 9/2008 |
| WO | 2008134544 | 11/2008 |
| WO | 2013126776 | 8/2013 |

OTHER PUBLICATIONS

PuraMatrix*, 3D Products Features, 1 pg., Last accessed Apr. 16, 2005, Japanese with English Abstract.
PuraMatrix*, 3D Product List, 1 pg., Last accessed Apr. 16, 2005, Japanese with English Abstract.
PuraMatrix*, 3D Introduction to Products,1 pg., Last accessed Apr. 16, 2005. Japanese with English Abstract.
"FDA Approves Sealant to Prevent Cerebrospinal Fluid Leaks After Brain Surgery." FDA U.S. Food and Drug Adminstration. Press Release.Available at http://www.fda.gov/NewsEvents/Newsroom/PressAnnouncements/2005/ucm108428.htm. Last accessed Jan. 28, 2011. 1 page.
Adler, "Self-assembling gel stops bleeding in seconds", New Scientist Tech.,1 (3):117 (Oct. 10, 2006).
Aggeli et at., "Self-assembling peptide polyelectrolyte beta-sheet complexes form nematic Hydrogels", Angew Chem Int Ed Eng. ,142(45):5603-6 (2003).
Ahmad, et al., "A novel hybrid system for the fabrication of a fibrous mesh with micro-inclusions", Carbohydr Polym., 89(1):222-9 (2012).
AlertNet, "Researches study liquid as tool to stop bleeding", www.alertnet.org, pp. 1, (Oct. 10, 2006).
Allen et at., "Variation of the axial haem ligands and haem-binding motif as a probe of the *Escherichia coli* c-type cytochrome maturation (Ccm) system", Biochem J., 375(Pt 3):721-8 (2003).
Atala, "Tissue engineering and regenerative medicine: concepts for clinical application", Rejuvenation Res. 7(1):15-31(2004).
Altman et al., "Conformational behavior of ionic self-complementary peptides", Protein Sci. 9(6): 1095-105 (2000).
Armstrong et al., "Blood flows within and among rat muscles as a function of time during high speed treadmill exercise", J Physiol, 344: 189-208 (1983).
Ball, "Brain Knitting", materials@nature.com, pp. 1-2 (2006).
Bansal, "Scientists develop liquid that could revolutionize bleeding control", All Headline News, pp. 1 (2006).
Barone, "Nanoliquid stops bleeding practically in a nanosecond", Discover Magazine, pp. 1 (Feb. 25, 2007), accessed Dec. 22, 2007.
BBC News, "Liquid to seal open wounds fast", www.newsvote.bbc.co.uk, pp. 1-3, (Oct. 14, 2006), accessed Jul. 10, 2009.
Benita, et al., "Characterization of drug-loaded poly(d,l-lactide) microspheres", J. Pharm. Sci., 73(12):1721-4 (1984).
Berendsen,"A Glimpse of the Holy Grail?" Science, 282: 642-643 (1998).
Bokhari et al., "The Enhancement of Osteoblast Growth and Differentiation in Vitro on a Peptide Hydrogel-PolyHIPE Polymer Hybrid Material," Biomaterials, 26:5198-208 (2005).
Bradley and Barrick, "Limits of Cooperativity in a Structurally Modular Protein: Response of the Notch Ankyrin Domain to Analogous Alanine Substitutions in Each Repeat," J. Mol. Biol., 324:373-86 (2002).
Brun, et al., "Electrospun scaffolds of self-assembling peptides with poly (ethylene oxide) for bone tissue engineering", Acta Biomater., 7:2526-32 (2011).
Bullis, "Nanohealing", Technology Review, pp. 1-3 (2007).
Caplan, et al., "Control of self-assembling oligopeptide matrix formation through systematic variation of amino acid sequence", Biomaterials, 23(1):219-27 (2002).
Caplan, et al., "Self-assembly of a beta-sheet protein governed by relief of electrostatic repulsion relative to van der Waals attraction", Biomacromolecules, 1:627-31 (2000).
Chemistry World, Pour-on Nanotechnology stops bleeding in seconds, http://www.rsc.org/chemistrvworld/News/2006/October/10080601., accessed Oct. 10, 2006.
Chen, "Self-assembly of ionic-complementary peptides: a physiochemical viewpoint", Colloids Surf A Physicochem Eng Asp., 261:3-24 (2005).
Chen, et al., "A hybrid silk/RADA-Based fibrous scaffold with triple hierarch for ligament regeneration", Tissue Eng, 18(13-14):1399-409 (2012).
Christie, "The nano-knitters", Popular Science, pp. 1, accessed Aug. 11, 2006.
Conform, definition from http://www.merriam-webster.com/dictionary/conform. pp. 1-2, accessed Aug. 4, 2009.
Crowston, et al., "New Optic Nerve? International Glaucoma Review", The Journal for the Glaucoma Society, (Meeting) Reports, pp. 1-2, (IGR 9-1 Jun. 2007).
Dahlberg, "Surgical discovery promising", The Sacramento Bee, pp. 1-3 (Oct. 10, 2006), accessed (Oct. 10, 2006).
Daily India, "Study: Biodegradable liquids halt bleeding", www.dailyindia.com; pp. 1, accessed Oct. 10, 2006.
Davis, et al., "Injectable self-assembling peptide nanofibers create intramyocardial microenvironments for endothelial cells", Circulation, 111 (4):442-50 (2005).
Deutschlandfunk, "Liquid plaster", www.dradio.de; pp. 1-2, (Oct. 11, 2006), accessed (Oct. 12, 2006).
Diaz, et al., "Are malignant cells displaced by large-gauge needle core biopsy of the breast", Am J Roentgenol 173(5):1303-13 (1999).
Ej, "Closing the CNS gap", ACS Chemical Biology, 1(3):116-22 (2006).
Ellis-Behnke, et al., "Crystal clear surgery with self-assembling molecules that act as a bio barrier in the brain and intetstine", Nanomedicine: Nanotechnology Biology and Medicine 1(3):269-70 (2005).
Ellis-Behnke, et al., "Molecular repair of the brain using self-assembling peptides", Chim. Oggi., 24(4) 42-45 (2006).
Ellis-Behnke, et al., "Molecular Restoration of the Body: Nano neuro knitting for brain repair", JEAAM & BAAMJ, 4:35-37 (2006).

(56) References Cited

OTHER PUBLICATIONS

Ellis-Behnke, et al., "Nano neuro knitting: peptide nanofiber scaffold for brain repair and axon regeneration with functional return of vision", PNAS, 103 (13):5054-9 (2006).
Ellis-Behnke, et al., "Using nanotechnology to design potential therapies for CNS regeneration", Curr. Pharm. Des., 13(24):2519-28 (2007).
Ellis-Behnke, et al. "Nano hemostat solution: immediate hemostasis at the nanoscale", Nanomedicine, 2:207-15 (2006).
Ellis-Behnke, et al., "Forever young; how to control the elongation, differentiation and proliferation of cells using nanotechnology", Cell Transplant, 18:1047-58 (2009).
Endometriosis, from Merck manual, pp. 1-5, Accessed Aug. 4, 2009.
Extended European Search Report for EP 10181924.1 mailed May 11, 2011.
Fox News, "New peptide salve could replace adhesive bandages", www.foxnews.com, pp. 1, (Oct. 10, 2006), accessed Oct. 10, 2006.
Frechet, "Dendrimers and supramolecular chemistry", PNAS, 99(8):4782-7 (2002).
Genove, et al., "The effect of functionalized self-assembling peptide scaffolds on human aortic endothelial cell function", Biomaterials, 26(16):3341-51 (2005).
Gibian, "Study: Biodegradable liquids halt bleeding", United Press International, (Oct. 10, 2006).
Gill, "Pour-on nanotechnology stops bleeding in seconds", Chemistry World, pp. 1-2, (2006).
Gruen et at., "Interaction of amino acids with silver(I) ions", Biochim Biophys Acta.,386(1):270-4 (1975).
Guo, et al., "Reknitting the injured spinal cord by self-assembling peptide nanofiber scaffold", Nanomedicine, 3(4):311-21 (2007).
Hampton, et al., "Healing power found in nano knitting", JAMA, 297(1):31 (2007).
Hartgerink, et al., "Nanomedicine: New material stops bleeding in a hurry", Nature Nanomedicine, 1(3): 166-7 (2006).
Hill, et al., "A field guide to foldamers", Chem. Rev., 101(12):3893-4012 (2001).
Hilton et al., "Wound dressings in diabetic foot disease", Clin Infect Dis., 39 Suppl 2:5100-3 (2004).
Holmes, et al., "Extensive neurite outgrowth and active synapse formation on self-assembling peptide scaffolds", PNAS, 97(12):6728-33 (2000).
Holtz, et al., "Growth factor stimulation reduces residual quiescent chronic myelogenous leukemia progenitors remaining after imatinib treatment", Cancer Res, 67(3):1113-20 (2007).
Hwang et at., "Self-assembling biomaterials: liquid crystal phases of cholesteryl oligo(L-tacticacid) and their interactions with cells", PNAS, 99(15):9662-7 (2002).
International Search Report and Written Opinion, mailed Aug. 7, 2008, PCT/US2007/010041.
International Search Report dated Sep. 28, 2006 in PCT/US2006/015850.
Intestinal Obstruction, from Merck manual, pp. 1-4, accessed Aug. 4, 2009.
Iran Daily, "Brain-healing bridges", www.iran-daily.com, pp. 1-2, accessed Apr. 25, 2006.
Kauvar, et at., "The epidemiology and modem management of traumatic hemorrhage: US and international perspectives", Crit Care, 9 Suppl 5:S 1-9 (2005).
Keloid and Hypertrophic Scar: Treatment and medication from http://emedicine.medscape.com/article/1057599-treatment, pp. 1-16, Accessed Aug. 4, 2009.
Keloids, from Merck manual, p. 1, Accessed Aug. 4, 2009.
Kendhale, et al., "Isotactic N-alkyl acrylamide oligomers assume self-assembled sheet structure: first unequivocal evidence from crystal structure", Chem Comm. (Camb), 26:2756-2758 (2006).
Khadka and Hayne, "Protein- and peptide-based electrospun nanofibers in medical biomaterials", Nanomedicine, 8:1242-62 (2012).
Kinsey et al., "Molecules in motion: influences of diffusion on metabolic structure and function in skeletal muscle", J Exp Biol., 214(Pt 2):263-74 (2011).
Knudsen, "Nanosolution halts bleeding", Technology Review, accessed Oct. 10, 2006.
Leon, et al., "Mechanical properties of a self-assembling oligopeptide matrix", J. Biomater. Sci Polym Ed., 9:297-312 (1998).
Ling, et al., "Id-1 expression promotes cell survival through activation of NF-kappaB signalling pathway in prostate cancer cells", Onogene, 22(29):4498-508 (2003).
Ma, et al., "Supramolecular polymer chemistry: self-assembling dendrimers using the DDA.AAD (GC-like) hydrogen bonding motif", J. Am. Chem. Soc., 124 (46):13757-69 (2002).
Marks, "Optic nerve regrown", New Scientist on www.stemcellschina.com, (Mar. 15, 2006), updated Jun. 29, 2006, accessed Aug. 11, 2006.
Mathiowitz and Langer, "Polyanhydride microspheres as drug carriers I. Hot-melt microencapsulation", J. Controlled Release, 5(1):13-22 (1987).
Mathiowitz, et al., "Morphology of polyanhydride microsphere delivery systems", Scanning Microscopy, 4(2):329-340 (1990).
Mathiowitz, et al., "Novel microcapsules for delivery systems", Reactive Polymers, 6:275-83 (1987).
Mathiowitz, et al., "Polyanhydride microspheres as drug carriers. 2. microencapsulation by solvent removal", J. Appl. Polymer Sci., 35, 755-774 (1988).
Mathiowitz, et al., "Polyanhydride microspheres. IV: Morphology and characterization of systems made by spray drying", J. Appl. Polymer Sci., 45:125-134 (1992).
Mishra, et al., "Ultrasmall natural peptides self-assemble to strong temperature-resistant helical fibers in scaffolds suitable for tissue engineering", Nano Today, 6 (3):232-9 (2011).
MIT News, "MIT material stops bleeding in seconds", www.web.mit.edu, pp. 1-2, Oct. 10, 2006, accessed Jul. 10, 2009.
Moore, et al., "A field guide to foldamers", Chem. Rev., 101(12), 3893-4012 (2001).
Mumbai Mirror, "New solution to stop bleeding", www.mumbaimirror.com; pp. 1 accessed Oct. 17, 2006.
Nano China, "Stopping bleeding", www.nanochina.cn, pp. 1-3, (Oct. 27, 2006), accessed Nov. 11, 2006.
Narmoneva, et al., "Self-assembling short oligopeptides and the promotion of angiogenesis", Biomaterials, 26(23):4837-46 (2005).
Newindpress, "New nano-gel that stops bleeding within seconds", www.newindpress.com, pp. 1, accessed Oct. 11, 2006.
News in Science, "Liquid stops bleeding during surgery", Reuters, pp. 1-2, accessedOct. 10, 2006.
Ngo et al.,"Computational Complexity, Protein Structure Prediction, and the Levinthal Paradox," The Protein Folding Problem and Tertiary Structure Prediction, K. Merc Jr. and S. Le Grand Edition, pp. 491-495 (1994).
Nguyen and Lee, "The effect of cross-linking on the microstructure, mechanical properties and biocompatibility of electrospun polycaprolactone-gelatin/PLGA-gelatin/PLGA-chitosan hybrid composite", Sci. Technol. Adv. Mater., 13:035002 (2012).
Palmer, "Peptide soup halts blood loss", Science NOW Daily News, pp. 1, Oct. 10, 2006.
Penland, "Recently discovered by researchers, a new liquid can stop bleeding faster than you can slap on a band-aid", Discover Magazine, Oct. 19, 2006.
Petrylak, et al., "Docetaxel and estramustine compared with mitoxantrone and prednisone for advanced refractory prostate cancer", N Eng J Med, 351 (15):1513-20 (2004).
Residue, definition from http://dictionary.reference.com/browse/residue. pp. 1-4, accessed Aug. 4, 2009.
Reya, et al., "Stem cells, cancer and cancer stem cells", Nature, 414 (6859):105-11 (2001).
Rudinger, "Characteristics of the amino acids as components of a peptide hormone sequence," Peptide Hormones, JA Parsons Edition, University Park Press, pp. 1-7(1976).
Sawhney, et al., "Bioerodible hydrogels based on photopolymerized poly (ethylene glycol)-co-poly(a-hydroxy acid) diacrylate macromers", Macromolecules, 26(4):581-587 (1993).

(56) References Cited

OTHER PUBLICATIONS

Science, Engineering and Technology, "Nanomaterial stops bleeding in seconds", www.scenta.co.uk, pp. 1-2, accessed Oct. 10, 2006.
Scientific American, "Protein gel stops bleeding in unknown way", www.sciam.com, pp. 1-2, accessed Oct. 10, 2006.
Schneider, et al., "Behavioral testing and preliminary analysis of the hamster visual system", Nat. Protoc., 1(4):1898-905 (2006).
Schinzel and Drueckes, "The phosphate recognition site of *Escherichia coli* maltodextrin phosphorylase," FEBS, 286(1,2): 125-128 (1991).
Scrivener, "Bleeding? Here\s a simple solution", Toronto Star, (Oct. 15, 2006).
Semino, et al., "Entrapment of migrating hippocampal neural cells in three-dimensional peptidenanofiber scaffold", Tissue Eng., 10(3-4):643-55 (2004).
Semino, et al., Functional differentiation of hepatocyte-like spheroid structures from putative liver progenitor cells in three-dimensional peptide scaffolds. Differentiation, 71 (4-5):262-70 (2003).
Sheihet, et at., "Hydrophobic drug delivery by self-assembling triblock copolymer-derived Nanospheres", Biomacromolecules,. 6(5):2726-31 (2005).
Shen et al., Artificial extracellular matrices can be used for in vitro control of stem cell differentiation. 2003 Summer Bioengineering Conference. Sonesta Beach Resort. Key Biscayne,Florida. Jun. 25-29, 2003: 1 page. Available at http://www.tulane.edu/(sbc2003/pdfdocs/0357..Retrieved on Apr. 27, 2011.
Tannock, et al., "Docetaxel plus prednisone or mitoxantrone plus prednisone for advanced prostate cancer", N Engl J Med., 351(15):1502-12 (2004).
Teather, et al., "Differential induction of c-Jun and Fos-like proteins in rat hippocampus and dorsal striatum after training in two water maze tasks", Neurobiol. Learn Mem., 84 (2):75-84 (2005).
Thomas, et al., "Nano neuro knitting repairs injured brain", Lancet Neurol., 5 (5):386 (2006).
Tortora, et al., "Skin Wound Healing." Principles of Human Anatomy 5th ed. 1989. 98-100.
Trafton, et al., "New material halts bleeding", MIT Tech Talk, 51(5): 1-3 (2006).
Tu and Tirrell, "Bottom-up design of biomimetic assemblies", Adv. Drug Deliv. Rev., 56(11):1537-63 (2004).
Tubal Dysfunction and Pelvic Lesions, from Merck manual, pp. 1-2, Accessed Aug. 4, 2009.
Voet and Voet, "Abnormal Hemoglobins", Biochemistry, Second Edition, John Wiley & Sons, Inc., pp. 235-241 (1995).
Water structure and science (retrieved from http://www.lsbu.ac.uk/water/molecule.html on Dec. 21, 2011 5 pages).
What\s Next in Science & Technology, "Biodegradable liquids can stop bleeding almost instantly—could significantly impact medicine", (Oct. 10, 2006), accessed Oct. 15, 2006.
Wilson, "Nano neuro-kit", Drug Discovery & Development, accessed Sep. 22, 2006.
Written Opinion dated Sep. 28, 2006 in PCT/US2006/015850.
Written Opinion for International Application No. PCT/US2008/057104, mailed Feb. 9, 2009.
Yokoi et al.,"Dynamic reassembly of peptide RADA16 nanofiber scaffold", PNAS, 102(24):8414-9 (2005).
Yung, et al., "Scientists discover new way to control bleeding", The Standard, pp. 1-2, (Oct. 11, 2006), accessed Oct. 10, 2006.
Zhang, et al., "Designer self-assembling peptide nanofiber scaffolds for 3D tissue cell cultures", Semin. Cancer Biol., 15(5):413-20 (2005).
Zhang, et al., "Peptide self-assembly in functional polymer science and engineering", Reactive & Functional Polymers, 41, 91-102 (1999).
Zhang et al., "Building from the bottom up",. Materials Today, pp. 20-27 (2003).
Zhang et al., "Emerging biological materials through molecular self-assembly", Biotechnology Advances, 20:321-39 (2002).
Zhang et at., "Self-assembling peptides in biology, materials science and engineering", Peptide Science—Present and Future,:737-44 (1999b).
Zhang, Designing novel materials and molecular machines. Economic Perspectives.:22-24. Available at http://www.esm.psu.edu/(ax14/1ak1itakia/Documents/ijee1005, Retrieved on Apr. 28, 2011 (2005b).
Zhang, et al., "Self-complementary oligopeptide matrices support mammalian cell attachment", Biomaterials, 16:1385-93 (1995).
Zhang, et al., "Spontaneous assembly of a self-complementary oligopeptide to form a stable macroscopic membrane", PNAS, 90:3334-8 (1993).
Zimmerman, et al., "Self-assembling dendrimers", Science, 271(5252):1095-8 (1996).

* cited by examiner

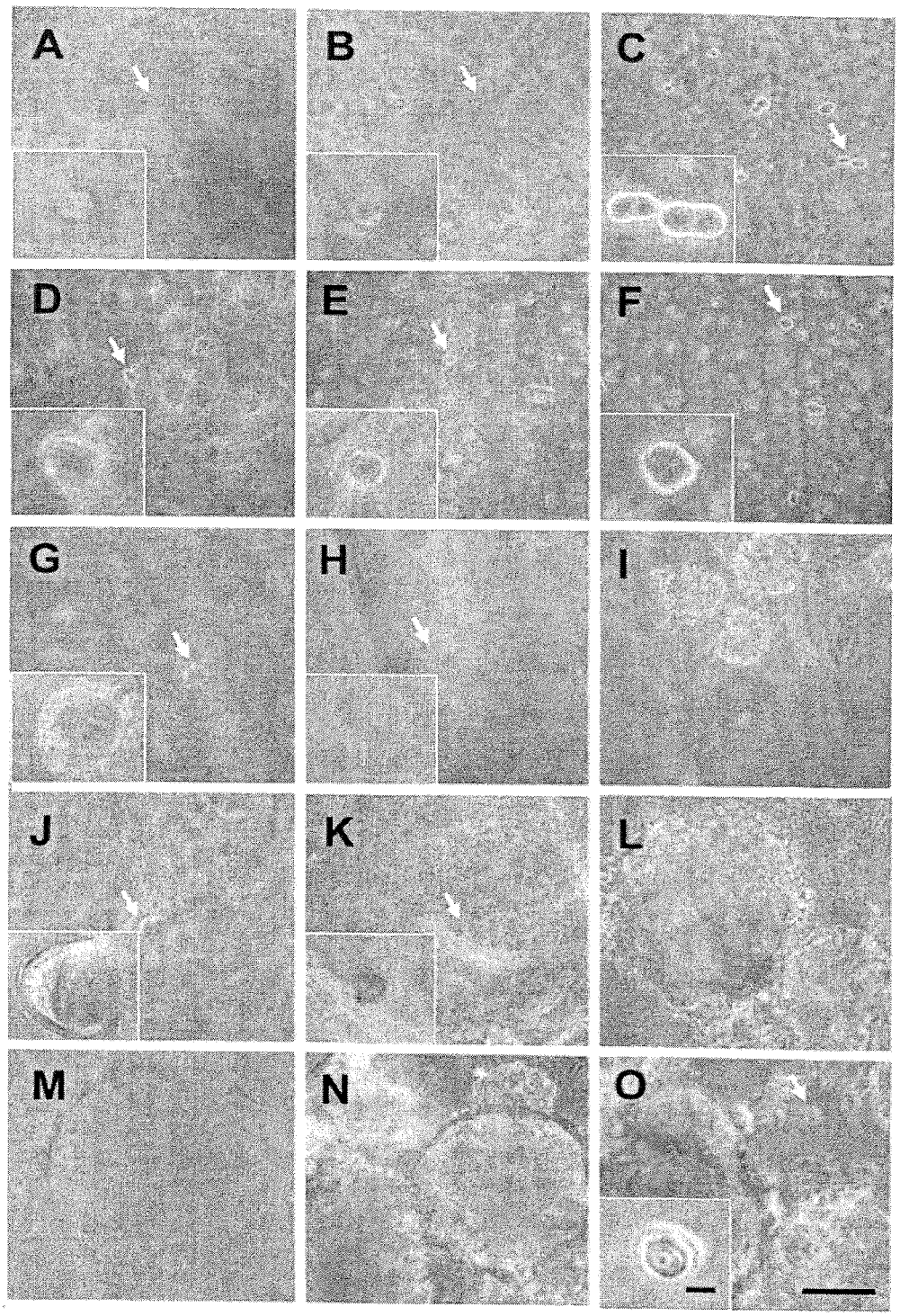

NANO CANCER BARRIER DEVICE (NCBD) TO IMMOBILIZE AND INHIBIT THE DIVISION OF METASTIC CANCER STEM CELLS

CROSS-REFERENCE TO RELATED APPLICATION

The subject application claims the benefit of U.S. Provisional Application Ser. No. 61/286,166, filed Dec. 14, 2009, which is incorporated herein by reference in its entirety.

BACKGROUND OF THE INVENTION

1. Field of the Invention

The present invention generally relates to the field of nanomaterials. More particularly, the present invention relates to treatment of cancer with self-assembling peptides.

2. Background Art

Prostate cancer (PCa) is responsible for the largest number of cancer deaths, with the exception of lung cancer. In the early stage, where the tumor is still localized, the disease can be cured by surgery or radioprostatectomy. However, due to the slow growing nature of the tumor, many PCa patients have already developed metastatic disease upon diagnosis and will inevitably enter the hormone refractory stage after hormone ablation therapy. There is currently no cure for hormone refractory prostate cancer (HRPC) at present. The most effective treatment regime for HRPC patients, Docetaxel-based chemotherapy, can only improve the median survival time for 3 months (12) (14). Therefore, effective treatment strategies against metastatic HRPC are urgently needed.

The reason that current therapies for metastatic HRPC fail is not completely understood. However, the isolation of cancer cells with stem-like characteristics provides solid evidence that prostate cancer stem cells (CSCs) may exist within the tumor. As in other types of cancer, prostate CSCs may account for the treatment failure; increasing evidence shows that current therapies are only successful in targeting the more differentiated tumor cells, sparing the putative cancer stem/progenitor cells (11). Like normal stem cells, CSCs are thought to be quiescent compared to mature cancer cells (7) (13) (6). This property makes CSCs resistance to chemotherapeutic drugs, which mainly target the actively replicating cells. The expression of multiple drug resistant gene (MDR1) (1) and ABC transporter (15) also help to protect the CSCs from cytotoxic drugs. In addition, prostate CSCs do not express androgen receptor; thus, they do not respond to hormone ablation in the same way as mature tumor cells. Therefore, elimination of the bulk of frequently replicating tumor cells, as well as the rare subset of slow dividing stem-like cells that are responsible for tumor regeneration, may represent a better therapeutic strategy in the treatment of PCa.

Due to their ability to self-renew and differentiate, prostate CSCs are capable of regenerating the heterogeneous tumor population (including both androgen-dependent and independent cells) and it is believed that CSCs may be responsible for the metastatic growth of primary prostate tumors (9). CSCs isolated from PCa cell lines have been found to be more invasive than the non-CSCs; likewise, PCa cells that are more invasive were found to possess stem cell characteristics. These results suggest that prostate CSCs may be the origin of prostate tumor metastasis and may be an ideal target for inhibiting disease metastasis. By limiting replication of CSCs, the progression of metastasis can be slowed. If the cells could be prevented from migrating away from the treatment area, it would allow for additional local targeting.

Previously, we demonstrated that by manipulating the cell density and concentration of the self-assembling peptide (SAP) material, we were able to control the proliferation, elongation, differentiation and maturation of cells in vitro. This included the nano environment surrounding PC12 cells, Schwann cells and neural precursor cells, as well as implants in the brain and spinal cord with and without cells (3). Here we show that prostate CSCs can be placed into stasis for an extended period of time without causing them to differentiate.

BRIEF SUMMARY

In one embodiment, the present invention provides a method for inhibiting cancer stem cell division by contacting the exterior of the cancer stem cell with at least one nanomaterial. In one aspect, contacting the exterior of the cancer stem cell with at least one nanomaterial will inhibit cancer stem cell colony formation. In one aspect, contacting the exterior of a cancer stem cell will cause inhibition of self-renewal of the cancer stem cell. In one aspect, contacting the exterior of a cancer stem cell will cause inhibition of spheroid formation from the cancer stem cell.

In one embodiment, the present invention provides a method for inhibiting metastasis of a cancer cell by introducing a plurality of self-assembling peptides to the exterior of the cancer cell. In one aspect, a method for inhibiting metastasis of cancer cells before, during, or after a surgical procedure involves introducing at least one nanomaterial at the area of surgical procedure and performing the surgical procedure, whereby the at least one nanomaterial surrounds the cancer cells and inhibits release of the cancer cells into the area of surgical procedure, inhibiting metastasis.

In one embodiment, the present invention provides a method for inhibiting progression of a tumor by contacting the tumor with at least one nanomaterial. In one aspect, a kit is provided for inhibiting cancer progression with at least one nanomaterial solution and at least one chemotherapeutic agent.

In one embodiment, the present invention provides a method for treatment of cancer by introducing at least one nanomaterial at the cancer. In one aspect, a method for treatment of cancer involves contacting the cancer with a plurality of self-assembling peptides.

In one embodiment, the present invention provides a composition comprising at least one nanomaterial that inhibits cancer cell division.

In one embodiment, the present invention provides a method for inducing a cell to go into stasis by contacting the exterior of the cell with at least one nanomaterial. In one aspect, a method is provided for inducing and maintaining stasis in cultured cells, the method involving seeding at least one cell in a vessel and contacting the at least one cell with at least one nanomaterial, causing the at least one nanomaterial to self-assemble around the at least one cell, resulting in stasis of the cell.

In one embodiment, the present invention provides a cell culture comprising at least one cell and at least one self-assembling peptide, wherein the at least one self-assembling peptide assembles around the at least one cell.

In one embodiment, the present invention provides a method for inhibiting bleeding during and after a surgical procedure, the method comprising introducing at least one nanomaterial at an area of surgical procedure. In one aspect, a method is provided for marking the margins of a tumor, the method comprising introducing at least one nanomaterial at the tumor, whereby the at least one nanomaterial self-assembles around the margins of the tumor, providing the marking for visualization of the tumor margins, thereby delineating its boundary.

BRIEF DESCRIPTION OF THE DRAWINGS

FIG. 1A-O shows pictures of prostate cancer stem cells at various time points during the experimental procedure. Day 1: cells in 1% SAP (A), 3% SAP (B), and control (C) on day 1. The insets are magnified images of the cells indicated by the arrows. Day 4: cells in 1% SAP (D), 3% SAP (E) and control (F) at day 4. Note the sizes of the cells are slightly larger in the 1% and 3% conditions, when compared to day 1 in the insets. Day 10: cells in 1% SAP (G), 3% SAP (H) and control (I) at day 10. In (I), the prostaspheres are clearly visible, while the two treatment conditions (G and H) are still single cells. Day 22: cells in 1% SAP (J), 3% SAP (K) and control (L) at day 22 with cells that are still in the SAP (insets), while the control (L) has clear prostasphere formation. Day 22 washed out: (M) and (N) are also at day 22 but are cells that have been washed out of the SAP. (M) cells were in 1% SAP and washed out at day 14; (N) cells were washed out of 3% SAP, also at day 14. Both have clear prostasphere formation. Day 28: (O) is at day 28 in 3% SAP with a prostasphere and a single cell that has remained in the SAP (arrow), still the same size as day 1 (inset). Scale bars are (inset) 5 microns and 100 microns.

DESCRIPTION OF THE SEQUENCES

SEQ ID NO: 1 is an amino acid sequence of a self-assembling peptide useful according to the subject invention.

SEQ ID NO: 2 is an amino acid sequence of a self-assembling peptide useful according to the subject invention.

SEQ ID NO: 3 is an amino acid sequence of a self-assembling peptide useful according to the subject invention.

SEQ ID NO: 4 is an amino acid sequence of a self-assembling peptide useful according to the subject invention.

SEQ ID NO: 5 is an amino acid sequence of a self-assembling peptide useful according to the subject invention.

SEQ ID NO: 6 is an amino acid sequence of a self-assembling peptide useful according to the subject invention.

SEQ ID NO: 7 is an amino acid sequence of a self-assembling peptide useful according to the subject invention.

SEQ ID NO: 8 is an amino acid sequence of a self-assembling peptide useful according to the subject invention.

SEQ ID NO: 9 is an amino acid sequence of a self-assembling peptide useful according to the subject invention.

SEQ ID NO: 10 is an amino acid sequence of a self-assembling peptide useful according to the subject invention.

SEQ ID NO: 11 is an amino acid sequence of a self-assembling peptide useful according to the subject invention.

SEQ ID NO: 12 is an amino acid sequence of a self-assembling peptide useful according to the subject invention.

SEQ ID NO: 13 is an amino acid sequence of a self-assembling peptide useful according to the subject invention.

SEQ ID NO: 14 is an amino acid sequence of a self-assembling peptide useful according to the subject invention.

SEQ ID NO: 15 is an amino acid sequence of a self-assembling peptide useful according to the subject invention.

SEQ ID NO: 16 is an amino acid sequence of a self-assembling peptide useful according to the subject invention.

SEQ ID NO: 17 is an amino acid sequence of a self-assembling peptide useful according to the subject invention.

SEQ ID NO: 18 is an amino acid sequence of a self-assembling peptide useful according to the subject invention.

SEQ ID NO: 19 is an amino acid sequence of a self-assembling peptide useful according to the subject invention.

SEQ ID NO: 20 is an amino acid sequence of a self-assembling peptide useful according to the subject invention.

SEQ ID NO: 21 is an amino acid sequence of a self-assembling peptide useful according to the subject invention.

SEQ ID NO: 22 is an amino acid sequence of a self-assembling peptide useful according to the subject invention.

SEQ ID NO: 23 is an amino acid sequence of a self-assembling peptide useful according to the subject invention.

SEQ ID NO: 24 is an amino acid sequence of a self-assembling peptide useful according to the subject invention.

SEQ ID NO: 25 is an amino acid sequence of a self-assembling peptide useful according to the subject invention.

SEQ ID NO: 26 is an amino acid sequence of a self-assembling peptide useful according to the subject invention.

SEQ ID NO: 27 is an amino acid sequence of a self-assembling peptide useful according to the subject invention.

SEQ ID NO: 28 is an amino acid sequence of a self-assembling peptide useful according to the subject invention.

SEQ ID NO: 29 is an amino acid sequence of a self-assembling peptide useful according to the subject invention.

SEQ ID NO: 30 is an amino acid sequence of a self-assembling peptide useful according to the subject invention.

SEQ ID NO: 31 is an amino acid sequence of a self-assembling peptide useful according to the subject invention.

SEQ ID NO: 32 is an amino acid sequence of a self-assembling peptide useful according to the subject invention.

SEQ ID NO: 33 is an amino acid sequence of a self-assembling peptide useful according to the subject invention.

SEQ ID NO: 34 is an amino acid sequence of a self-assembling peptide useful according to the subject invention.

SEQ ID NO: 35 is an amino acid sequence of a self-assembling peptide useful according to the subject invention.

SEQ ID NO: 36 is an amino acid sequence of a self-assembling peptide useful according to the subject invention.

SEQ ID NO: 37 is an amino acid sequence of a self-assembling peptide useful according to the subject invention.

SEQ ID NO: 38 is an amino acid sequence of a self-assembling peptide useful according to the subject invention.

SEQ ID NO: 39 is an amino acid sequence of a self-assembling peptide useful according to the subject invention.

SEQ ID NO: 40 is an amino acid sequence of a self-assembling peptide useful according to the subject invention.

SEQ ID NO: 41 is an amino acid sequence of a self-assembling peptide useful according to the subject invention.

SEQ ID NO: 42 is an amino acid sequence of a self-assembling peptide useful according to the subject invention.

SEQ ID NO: 43 is an amino acid sequence of a self-assembling peptide useful according to the subject invention.

SEQ ID NO: 44 is an amino acid sequence of a self-assembling peptide useful according to the subject invention.

SEQ ID NO: 45 is an amino acid sequence of a self-assembling peptide useful according to the subject invention.

SEQ ID NO: 46 is an amino acid sequence of a self-assembling peptide useful according to the subject invention.

SEQ ID NO: 47 is an amino acid sequence of a self-assembling peptide useful according to the subject invention.

SEQ ID NO: 48 is an amino acid sequence of a self-assembling peptide useful according to the subject invention.

SEQ ID NO: 49 is an amino acid sequence of a self-assembling peptide useful according to the subject invention.

SEQ ID NO: 50 is an amino acid sequence of a self-assembling peptide useful according to the subject invention.

SEQ ID NO: 51 is an amino acid sequence of a self-assembling peptide useful according to the subject invention.

SEQ ID NO: 52 is an amino acid sequence of a self-assembling peptide useful according to the subject invention.

SEQ ID NO: 53 is an amino acid sequence of a self-assembling peptide useful according to the subject invention.

SEQ ID NO: 54 is an amino acid sequence of a self-assembling peptide useful according to the subject invention.

SEQ ID NO: 55 is an amino acid sequence of a self-assembling peptide useful according to the subject invention.

SEQ ID NO: 56 is an amino acid sequence of a self-assembling peptide useful according to the subject invention.

SEQ ID NO: 57 is an amino acid sequence of a self-assembling peptide useful according to the subject invention.

SEQ ID NO: 58 is an amino acid sequence of a self-assembling peptide useful according to the subject invention.

SEQ ID NO: 59 is an amino acid sequence of a self-assembling peptide useful according to the subject invention.

SEQ ID NO: 60 is an amino acid sequence of a self-assembling peptide useful according to the subject invention.

SEQ ID NO: 61 is an amino acid sequence of a self-assembling peptide useful according to the subject invention.

SEQ ID NO: 62 is an amino acid sequence of a self-assembling peptide useful according to the subject invention.

SEQ ID NO: 63 is an amino acid sequence of a self-assembling peptide useful according to the subject invention.

SEQ ID NO: 64 is an amino acid sequence of a self-assembling peptide useful according to the subject invention.

SEQ ID NO: 65 is an amino acid sequence of a self-assembling peptide useful according to the subject invention.

SEQ ID NO: 66 is an amino acid sequence of a self-assembling peptide useful according to the subject invention.

SEQ ID NO: 67 is an amino acid sequence of a self-assembling peptide useful according to the subject invention.

SEQ ID NO: 68 is an amino acid sequence of a self-assembling peptide useful according to the subject invention.

SEQ ID NO: 69 is an amino acid sequence of a self-assembling peptide useful according to the subject invention.

SEQ ID NO: 70 is an amino acid sequence of a self-assembling peptide useful according to the subject invention.

SEQ ID NO: 71 is an amino acid sequence of a self-assembling peptide useful according to the subject invention.

SEQ ID NO: 72 is an amino acid sequence of a self-assembling peptide useful according to the subject invention.

SEQ ID NO: 73 is an amino acid sequence of a self-assembling peptide useful according to the subject invention.

SEQ ID NO: 74 is an amino acid sequence of a self-assembling peptide useful according to the subject invention.

SEQ ID NO: 75 is an amino acid sequence of a self-assembling peptide useful according to the subject invention.

SEQ ID NO: 76 is an amino acid sequence of a self-assembling peptide useful according to the subject invention.

DETAILED DESCRIPTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described, or referenced herein, are well understood and commonly employed using conventional methodology by those skilled in the art. As appropriate, procedures involving the use of commercially available kits and reagents are generally carried out in accordance with manufacturer defined protocols and/or parameters unless otherwise noted.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

The term "at the cancer," as used herein in the specification and in the claims, refers to the location immediately surrounding a cancer, adjacent to the cell membranes or surrounding extra-cellular matrix.

The term "chemotherapeutic agent," as used herein in the specification and in the claims, refers to a substance that inhibits or prevents the expression activity of cells, function of cells and/or causes destruction of cells. The term is intended to include radioactive isotopes and toxins, such as small molecule toxins or enzymatically active toxins of bacterial, fungal, plant or animal origin, including fragments and/or variants thereof. Examples of cytotoxic agents include, but are not limited to, maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other agents, such as alkylating agents, antimetabolites, anthracyclines, plant alkaloids, topoisomerase inhibitors, or other antitumor agents. Chemotherapeutic agents, as used in the embodiments of the present invention, can also include radioisotopes, such as At211, I131, I125, Y90, Re186, Re188, Sm153, Bi212, P32 and radioactive isotopes of Lu and antibodies possibly conjugated to an anti-cancer pro-drug activating enzyme capable of converting the pro-drug to its active form.

The term "cancer stem cell" or "CSCs," as used herein in the specification and in the claims, refers to cancer cells found within tumors that possess similar characteristics as normal stem cells (i.e. the ability to give rise to all cell types found in a particular tumor—making CSCs tumorigenic). It is hypothesized by many scientists that CSCs are present in a large number of, if not all, tumor types. CSCs have been shown in leukemia and, at least in the following, solid tumor cancers: brain, breast, colon, ovarian, pancreatic, and prostate. CSCs may generate tumors through the stem cell processes of self-renewal and differentiation into various cell types. Such cells are proposed to persist in tumors as a distinct population and possibly cause metastasis. CSCs also form cancer stem cell colonies in cell culture conditions.

The term "contacting," as used herein in the specification and claims, refers to placing the nanomaterial, composition, or other chemicals or agents such that the targeted cells are in contact with the nanomaterial, composition, or other chemicals or agents. When contacting a tumor, the nanomaterial, composition, or other chemicals or agents may be released inside and/or on the outside of the tumor such that cells in the interior of the tumor are targeted as well. The nanomaterial, composition, or other chemicals or agents of the present invention may be introduced, or seeded, at the targeted area, cell or tumor by various methods known to those skilled in the art. Such methods may include, but are not limited to, injection into or proximal to the targeted area, cell or tumor; injection at a position distal to the targeted area, cell or tumor; and direct contact with the targeted area, cell or tumor by other means, such as pouring, spraying, or painting the material onto the surface of the targeted area, cell or tumor. Means of injecting material in the present invention can include injection by needles, pipets, catheters or any other surgical means known by those skilled in the art. If contacting cells or tumors in cell culture conditions, any method of seeding materials onto culture dishes may be used, such as, but not limited to, pouring, pipetting, microinjecting or spraying.

The term "effective amount" or "therapeutically effective amount" or "therapeutically effective dosage," as used herein in the specification and claims, in general means the amount that, when administered to a subject for treating a disease (e.g. cancer), is sufficient to affect the desired degree of treatment for the disease. In general, such an amount or dosage preferably inhibits, reduces, disrupts, or treats a disease by at least 10%, more preferably by at least 40%, even more preferably by at least 60%, and still more preferably by at least 80%, relative to an untreated subject.

The term "exterior," as used herein in the specification and in the claims, refers to the outside of a cell or tumor or tissue or organ. In relation to a cell, the term refers to the cell membrane. In relation to a tumor or tissue or organ, the term refers to the region immediately adjacent to the targeted tumor, tissue, or organ, which can include contact with the cell membrane of individual cells of the tumor, tissue, or organ; or it can include contact with the extra-cellular matrix surrounding the tumor, tissue, or organ. In the event the cell membrane or extra-cellular matrix of a cell, tissue, organ or tumor is breached by any surgical or non-surgical occurrence, the exterior would include the areas resultantly exposed to the outside environment.

The term "inhibiting" or "inhibit," as used herein in the specification and in the claims, refers to the ability of the elements of the methods, kits, or compositions of the present invention to suppress and/or stop cell division, colony formation, metastasis, tumor progression, self-renewal, spheroid formation, bleeding or other cell processes and functions.

The term "label" or "labeled" or "molecular label" or "tag," as used herein in the specification and claims, can be used interchangeably and refer to incorporation or attachment, optionally covalently or non-covalently, of a detectable marker into a molecule, such as polypeptides or self-assembling peptides. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "metastasis" or "metastatic disease," as used herein in the specification and in the claims, refers to the spread of a cancer from one organ or tissue to another non-adjacent organ or tissue. Cancer cells can break away, leak, or spill from a primary tumor and enter lymphatic and blood vessels, circulate throughout the bloodstream, and be deposited elsewhere in the body. This occurrence is referred to as "metastasis." Metastasis is one of the hallmarks of malignancy of cancers.

The term "nanomaterial," as used herein in the specification and claims, is any nano scale material having multiple sites capable of interacting with biological systems in a well-controlled manner. The interactions can be covalent, ionic, dipolar, apolar, or a mixture or a combination of such interactions. Such materials have broad application in a number of fields and industries. These nanomaterials exhibit unique properties and functions in addition to their small size. Examples of such materials include, without limitation, self-assembling peptides, boron-nitride nanostructures, carbon nanostructures, dendrimers, oligomers and polymers with multiple functional groups, metal oxide nanostructures (e.g., FeO, $SiO_2$, $Al_2O_3$, $TiO_2$, ZnO, aluminosilicates, silicoaluminates, quantum dots (e.g., CdSe), etc.), metal clusters (e.g., non-transition metals, transition metals, actinide metals, lanthanide metals, etc. or mixed metal clusters), nanoshells (e.g., metal coated dielectric nanoparticles, metal coated metal nanoparticles, etc.), liposomes, or mixtures of combinations thereof. "Nanomaterials" as used herein can also refer to biomaterials (such as bionanoparticles) have been explored as building blocks for nanomaterial development. Bionanoparticles, including, but not limited to, virus and viral like particles, ferritins, self-assembling peptides and other self-assembled protein cages, are highly ordered nano-scale biological structures generated by nature. For example, viruses are generally composed of genetic material contained within a protective protein shell, sometimes referred to as the capsid. A capsid is composed of proteins encoded by the viral genome and its shape serves as the basis for morphological distinction.

The nanomaterials, for purposes herein, may be used in a liquid, powder, or slurry mixture. In one embodiment, the nanomaterial is provided as a dry or lyophilized powder which can be administered directly as a powder or a tablet, disk or wafer, which hydrates at the site of application, or suspended or dissolved in a liquid (e.g. aqueous liquid), and applied as a spray, paint, or injection or a hydrogel, including a material such as chitin, collagen, alginate, or synthetic polymer. In one embodiment, the nanomaterial is provided in combination with an oil, and forms a laminate. In one embodiment, the nanomaterial is provided in a bandage, foam, gel, paste, cream, ointment or matrix, in which the nanomaterial may be dispersed or absorbed.

The term "peptide," as used herein in the specification and claims, includes "polypeptide," "oligopeptide," and "protein" and refers to a string of at least two amino acid residues linked together by covalent bonds (e.g., peptide bonds). Useful peptides can vary in length so long as they retain the ability to self-assemble to an extent useful for one or more of the purposes described herein. Peptides having as few as two amino acid residues or as many as approximately 200 residues, and, those recognized to self-assemble, typically have a length within this range (e.g., 8-200, 8-36, 8-24, 8-16, 12-20, 6-64, or 16-20 amino acid residues). Depending on the context, "peptide" may refer to an individual peptide or to a collection of peptides having the same or different sequences. In addition, one or more of the amino acid residues in a self-assembling peptide (SAP) can be altered, or a derivative produced, by the addition of a chemical entity, such as an acyl group, a carbohydrate group, a carbohydrate chain, a phosphate group, a farnesyl group, an isofarnesyl group, a fatty acid group, or a linker for conjugation or functionalization (i.e. tags or markers). Useful peptides can also be branched, in which case they will contain at least two amino acid polymers, each of which consists of at least three amino acid residues joined by peptide bonds. The two amino acid polymers themselves are linked, but not by a peptide bond.

While the sequences of the peptides can vary, useful sequences include those that convey an amphiphilic nature to the peptides (e.g., the peptides can include approximately equal numbers of hydrophobic and hydrophilic amino acid residues), and the peptides can be complementary and structurally compatible. Complementary peptides have an ability to interact through ionic or hydrogen bonds that form between residues (e.g., hydrophilic residues) on adjacent peptides in a structure. For example, a given hydrophilic residue in a peptide can either hydrogen bond or ionically pair with a hydrophilic residue on an adjacent peptide. Unpaired residues can be exposed to the solvent. Peptide-peptide interaction may also involve van der Waals forces or other forces that do not constitute covalent bonds. The peptides are structurally compatible when they are capable of maintaining a sufficiently constant intrapeptide distance to allow assembly and structure formation. While the intrapeptide distance can vary, it can be quite small (e.g., less than about 4, 3, 2, or 1 Å). The intrapeptide distance (e.g., an average of a representative number of distances) can be larger than this, however. These distances can be calculated based on molecular modeling or based on a simplified procedure that has been previously reported (see U.S. Pat. No. 5,670,483).

More specifically, the peptides can have, or can include, a sequence of amino acid residues conforming to one or more of Formulas I-IV:

$$((Xaa^{neu}\text{-}Xaa^+)_x(Xaa^{neu}\text{-}Xaa^-)_y)_n \quad (I)$$

$$((Xaa^{neu}\text{-}Xaa^-)_x(Xaa^{neu}\text{-}Xaa^+)_y)_n \quad (II)$$

$$((Xaa^+\text{-}Xaa^{neu})_x(Xaa^-Xaa^{neu})_y)_n \quad (III)$$

$$((Xaa^-\text{-}Xaa^{neu})_x(Xaa^+Xaa^{neu})_y)_n \quad (IV)$$

where: $Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2 or 4, independently; and n is an integer having a value of 1-10 (e.g., 1-8, 1-5, or 1-3).

The self-assembling peptides can have a sequence of amino acid residues where $Xaa^{neu}$ represents alanine, valine, leucine, isoleucine, or glycine; $Xaa^+$ represents arginine, lysine or histidine; and $Xaa^-$ represents aspartic acid or glutamic acid. For example, the self-assembling peptides can have, or can include, the amino acid sequence RADARADARADA (SEQ ID No: 31). Other examples include ARADARADARAD (SEQ ID NO: 32); AKADAKADAKAD (SEQ ID NO: 33); AHADAHADA-HAD (SEQ ID NO: 34); ARAEARAEARAE (SEQ ID NO: 35); AKAEAKAEAKAE (SEQ ID NO: 36); and AHAE-AHAEAHAE (SEQ ID NO: 37).

The structures described herein can be formed through self-assembly of the peptides described in U.S. Pat. Nos. 5,670,483; 5,955,343; 6,548,630; and 6,800,481 and in Holmes et al., *Proc. Natl. Acad. Sci. USA*, 97:6728-6733 (2000); Zhang et al., *Proc. Natl. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 9:297-312 (1998); and Caplan et al., *Biomacromolecules*, 1:627-631 (2000). Representative self-assembling peptides are shown in Table 1.

TABLE 1

Representative Self-Assembling Peptides

| Name | Sequence (n-->c) | Modulus | |
|---|---|---|---|
| RADA16-I | n-RADARADARADARADA-c | I | (SEQ ID NO: 1) |
| RGDA16-I | n-RADARGDARADARGDA-c | I | (SEQ ID NO: 2) |
| RADA8-I | n-RADARADA-c | I | (SEQ ID NO: 3) |
| RAD16-II | n-RARADADARARADADA-c | II | (SEQ ID NO: 4) |
| RAD8-II | n-RARADADA-c | II | (SEQ ID NO: 5) |
| EAKA16-I | n-AEAKAEAKAEAKAEAK-c | I | (SEQ ID NO: 6) |
| EAKA8-I | n-AEAKAEAK-c | I | (SEQ ID NO: 7) |
| RAEA16-I | n-RAEARAEARAEARAEA-c | I | (SEQ ID NO: 8) |
| RAEA8-I | n-RAEARAEA-c | I | (SEQ ID NO: 9) |
| KADA16-I | n-KADAKADAKADAKADA-c | I | (SEQ ID NO: 10) |
| KADA8-I | n-KADAKADA-c | I | (SEQ ID NO: 11) |
| EAH16-II | n-AEAEAHAHAEAEAHAH-c | II | (SEQ ID NO: 12) |
| EAH8-II | n-AEAEAHAH-c | II | (SEQ ID NO: 13) |
| EFK16-II | n-FEFEFKFKFEFEFKFK-c | II | (SEQ ID NO: 14) |
| EFK8-II | n-FEFKFEFK-c | I | (SEQ ID NO: 15) |
| ELK16-II | n-LELELKLKLELELKLK-c | II | (SEQ ID NO: 16) |
| ELK8-II | n-LELELKLK-c | II | (SEQ ID NO: 17) |
| EAK16-II | n-AEAEAKAKAEAEAKAK-c | II | (SEQ ID NO: 18) |
| EAK12 | n-AEAEAEAEAKAK-c | IV/II | (SEQ ID NO: 19) |
| EAK8-II | n-AEAEAKAK-c | II | (SEQ ID NO: 20) |
| KAE16-IV | n-KAKAKAKAEAEAEAEA-c | IV | (SEQ ID NO: 21) |
| EAK16-IV | n-AEAEAEAEAKAKAKAK-c | IV | (SEQ ID NO: 22) |
| RAD16-IV | n-RARARARADADADADA-c | IV | (SEQ ID NO: 23) |
| DAR16-IV | n-ADADADADARARARAR-c | IV | (SEQ ID NO: 24) |
| DAR16-IV* | n-DADADADARARARARA-c | IV | (SEQ ID NO: 25) |
| DAR32-IV | n-(ADADADADARARARAR)-c | IV | (SEQ ID NO: 26) |

TABLE 1-continued

Representative Self-Assembling Peptides

| Name | Sequence (n-->c) | Modulus | |
|---|---|---|---|
| EHK16 | n-HEHEHKHKHEHEHKHK-c | N/A | (SEQ ID NO: 27) |
| EHK8-I | n-HEHEHKHK-c | N/A | (SEQ ID NO: 28) |
| VE20* | n-VEVEVEVEVEVEVEVEVEVE-c | N/A | (SEQ ID NO: 29) |
| RF20* | n-RFRFRFRFRFRFRFRFRFRF-c | N/A | (SEQ ID NO: 30) |
| RAD12-I | n-RADARADARADA-c | I | (SEQ ID NO: 31) |
| | n-AKAKAEAEAKAKAEAE-c | | (SEQ ID NO: 38) |
| | n-AKAEAKAEAKAEAKAE-c | | (SEQ ID NO: 39) |
| | n-EAKAEAKAEAKAEAKA-c | | (SEQ ID NO: 40) |
| | n-KAEAKAEAKAEAKAEA-c | | (SEQ ID NO: 41) |
| | n-ADADARARADADARAR-c | | (SEQ ID NO: 42) |
| | n-ARADARADARADARAD-c | | (SEQ ID NO: 43) |
| | n-DARADARADARADARA-c | | (SEQ ID NO: 44) |
| | n-ADARADARADARADAR-c | | (SEQ ID NO: 45) |
| | n-ARADAKAEARADAKAE-c | | (SEQ ID NO: 46) |
| | n-AKAEARADAKAEARAD-c | | (SEQ ID NO: 47) |
| | n-ARAKADAEARAKADAE-c | | (SEQ ID NO: 48) |
| | n-AKARAEADAKARADAE-c | | (SEQ ID NO. 49) |
| | n-AQAQAQAQAQAQAQAQ-c | | (SEQ ID NO: 50) |
| | n-VQVQVQVQVQVQVQVQ-c | | (SEQ ID NO: 51) |
| | n-YQYQYQYQYQYQYQYQ-c | | (SEQ ID NO: 52) |
| | n-HQHQHQHQHQHQHQHQ-c | | (SEQ ID NO: 53) |
| | n-ANANANANANANANAN-c | | (SEQ ID NO: 54) |
| | n-VNVNVNVNVNVNVNVN-c | | (SEQ ID NO: 55) |
| | n-YNYNYNYNYNYNYNYN-c | | (SEQ ID NO: 56) |
| | n-HNHNHNHNHNHNHNHN-c | | (SEQ ID NO: 57) |
| | n-ANAQANAQANAQANAQ-c | | (SEQ ID NO: 58) |
| | n-AQANAQANAQANAQAN-c | | (SEQ ID NO: 59) |
| | n-VNVQVNVQVNVQVNVQ-c | | (SEQ ID NO: 60) |
| | n-VQVNVQVNVQVNVQVN-c | | (SEQ ID NO: 61) |
| | n-YNYQYNYQYNYQYNYQ-c | | (SEQ ID NO: 62) |
| | n-YQYNYQYNYQYNYQYN-c | | (SEQ ID NO: 63) |
| | n-HNHQHNHQHNHQHNHQ-c | | (SEQ ID NO: 64) |
| | n-HQHNHQHNHQHNHQHN-c | | (SEQ ID NO: 65) |
| | n-AKAQADAKAQADAKAQAD-c | | (SEQ ID NO: 66) |
| | n-VKVQVDVKVQVDVKVQVD-c | | (SEQ ID NO: 67) |
| | n-YKYQYDYKYQYDYKYQYD-c | | (SEQ ID NO: 68) |
| | n-HKHQHDHKHQHDHKHQHD-c | | (SEQ ID NO: 69) |
| | n-ADADAKAKADADAKAK-c | | (SEQ ID NO: 70) |

TABLE 1-continued

Representative Self-Assembling Peptides

| Name | Sequence (n-->c) | Modulus | |
|------|------------------|---------|---|
| | n-KAKAKAKAKAKAKA-c | (SEQ ID NO: 71) | |
| | n-EAEAEAEAEAEAEAEA-c | (SEQ ID NO: 72) | |
| | n-ADADADADADADADAD-c | (SEQ ID NO: 73) | |
| | n-ARARADADARARADAD-c | (SEQ ID NO: 74) | |
| | n-VRVRVDVDVRVRVDVD-c | (SEQ ID NO: 75) | |

N/A denotes not applicable
*These peptides form a β-sheet when incubated in a solution containing NaCl, however they have not been observed to self-assemble to form macroscopic structures.

Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another by the formation of disulfide bonds. Structures bonded in this manner may have increased mechanical strength relative to structures made with comparable peptides that do not include cysteine residues.

One class of materials that can be used in connection with the invention are peptidomimetics. Peptidomimetics, as used herein, refers to molecules which mimic peptide structure. Peptidomimetics have general features analogous to their parent structures, polypeptides, such as amphiphilicity. Examples of such peptidomimetic materials are described in Moore et al., Chem. Rev. 101(12), 3893-4012 (2001).

Peptidomimetic materials of the invention can include (α-peptides, β-peptides, γ-peptides, and δ-peptides. Copolymers of these peptides can also be used. Examples of α-peptide peptidomimetics include, but are not limited to, N,N'-linked oligoureas, oligopyrrolinones, oxazolidin-2-ones, azatides and azapeptides.

Examples of suitable β-peptides include, but are not limited to, β-peptide foldamers, α-aminoxy acids, sulfur-containing β-peptide analogues, and hydrazino peptides.

Examples of suitable γ-peptides include, but are not limited to, γ-peptide foldamers, oligoureas, oligocarbamates, and phosphodiesters.

Examples of suitable δ-peptides include, but are not limited to, alkene-based δ-amino acids and carbopeptoids, such as pyranose-based carbopeptoids and furanose-based carbopeptoids.

Another class of molecules which can be used in the invention, and can in some instances self assemble, are nucleotidomimetics, such as isomeric oligonucleotides, modified carbohydrates, nucleotides with modified nucleotide linkages, and nucleotides with alternative nucleobases.

Examples of suitable isomeric nucleotides include, but are not limited to, iso-RNA and iso-DNA and α-DNA (change in the anomeric configuration from β to α), alt-DNA, and 1-DNA.

Examples of suitable modified carbohydrates include, but are not limited to, backbones with C 1'-bases connectivities such as tetrofuranosyl oligonucleotides, pentopyranosyl oligonucleotides, and hexopyranosyl oligonucleotides; backbones with C2'-base connectivities such as isonucleotides (repositioning of the base sugar connection from C1 to the C2 position), HNAs (insertion of an additional methylene group between the 04' and C 1' position of a furanose), ANAs (incorporation of a C3'-(S)-hydroxyl group), MNAs (inversion of the C3'-OH configuration from (S) in ANAs to (R)), CNAs (replacement of the 0 of the hexose with a methylene group), CeNAs (introduction of a 5'-6' alkene within the analogous ring), as well as other ring systems, torsionally restricted oligonucleotides such as bicyclic oligonucleotides, LNAs (restriction of the pentofaranose backbone to the 3'-endo configuration), torsionally flexible oligonucleotides such as base sugar extensions (insertion of methylene and ethylene groups into both α- and β-deoxynucleotides) and acyclic backbones (glycerol derivatives incorporating phosphodiester linkages).

Examples of nucleotides with modified nucleotide linkages include, but are not limited to, PNAs (peptide nucleic acids), NDPs (nucleo-δ-peptides), fused sugar-base backbones, and cationic linkages.

Examples of suitable alternative nucleobases include, but are not limited to, nucleotides with alternative aromatic nucleobases.

Another class of compounds useful in connection with the invention includes oligomers having backbones which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of suitable compounds containing backbones utilizing bipyridine segments include, but are not limited to, oligo(pyridine-pyrimidines), oligo(pyridine-pyrimidines) with hydrazal linkers, and pyridine-pyridazines.

Examples of suitable compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of suitable compounds containing backbones utilizing side chain interactions include, but are not limited to, oligothiophenes such as olihothiophenes with chiral p-phenyl-oxazoline side chains, and oligo(m-phenylene-ethynylene)s.

Examples of compound containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of suitable compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-pheylene ethynylene)s containing metal-coordinating cyano groups, and hexapyrrins.

Other materials which can self-assemble or can otherwise be useful in the invention include N-alkylacrylamide oligomers and di- and triblock co-polymers. N-alkylacrylamides can assume self-assembled sheet-like structures. Examples of suitable block copolymers include copolypeptides, polypeptide-PEGS, PEO-polybutadienes, PEG-polysaccharides, etc.

The amino acid residues in the self-assembling peptides can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrolysine or selenocysteine). Non-naturally occurring amino acids have not been found in nature, but can be incorporated into a peptide chain. These include D-alloisoleucine(2R,3S)-2-amino-3-methylpentanoic acid, L-cyclopentyl glycine (S)-2-amino-2-cyclopentyl acetic acid. For other examples, one can consult textbooks or the worldwide web (a site is maintained by the California Institute of Technology and displays structures of non-natural amino acids that have been successfully incorporated into functional proteins). Non-natural amino acid residues and amino acid derivatives listed in U.S. Application No. 20040204561 can be used. Self-assembling peptides can be chemically synthesized or purified from natural or recombinantly-produced sources by methods well known in the art. For example, peptides can be synthesized using standard f-moc chemistry and purified using high pressure liquid chromatography (HPLC). Such non-naturally occurring amino acids could be useful as self-assembling peptides or in combination with other self-assembling peptides and nanomaterials.

Where self-assembling peptides are used, it is thought that their side-chains (or R groups) partition into two faces, a polar face with positively and/or negatively charged ionic side chains, and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides may therefore be called ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residue alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV." A peptide having four repeating units of the sequence EAKA may be designated EAKA16-I, and peptides having other sequences may be described by the same convention.

Self-complementary peptides, such as EAKA 16-I, RADA16-I, RAEA16-I, and KADA16-I, are described in Table 1. Peptides with modulus I (i.e., peptides having alternate positively and negatively charged R groups on one side (e.g., the polar face) of the β-sheet) are described by each of Formulas I-IV, where x and y are 1. Peptides of modulus II (i.e., peptides having two residues bearing one type of charge (e.g., a positive charge) followed by two residues bearing another type of charge (e.g., a negative charge) are described by the same formulas where both x and y are 2. Peptides of modulus III have (i.e. peptides having three residues bearing one type of charge (e.g., a positive charge) followed by three residues bearing another type of charge (e.g., a negative charge) such as RARARA-DADADA (SEQ ID NO: 76).

Modulus IV ionic self-complementary peptides containing 16 amino acids; such as EAK16-IV, KAE16-IV, DAR16-IV, and RAD16-IV have also been studied. If the charged residues in these self-assembling peptides are substituted (e.g., the positively charged lysines are replaced by positively charged arginines and the negatively charged glutamates are replaced by negatively charged aspartates), there are essentially no known significant effects on the self-assembly process. However, if the positively charged residues (lysine and arginine) are replaced by negatively charged residues (aspartate and glutamate), the peptides can no longer undergo self-assembly to form macroscopic structures. However, they can still form a beta-sheet structure in the presence of a salt. Other hydrophilic residues that form hydrogen bonds, such as asparagine and glutamine, may be incorporated into the peptides instead of, or in addition to, charged residues. If the alanine residues in the peptides are changed to more hydrophobic residues, such as leucine, isoleucine, phenylalanine or tyrosine, the resulting peptides have a greater tendency to self-assemble and foam peptide matrices with enhanced strength. Some peptides that have similar amino acids compositions and lengths as the peptides described here form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays. Peptide-based structures can be formed of heterogeneous mixtures of peptides (i.e., mixtures containing more than one type of peptide conforming to a given formula or to two or more of the formulas). In some embodiments, each of the types of peptides in the mixture is able to self-assemble alone. In other embodiments, one or more of each type of peptide would not, alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides, which are complementary and structurally compatible to each other, can be used. For example, mixtures of KAKAKAKAKAKAKAKA (SEQ ID NO: 71) and EAE-AEAEAEAEAEAEA (SEQ ID NO: 72) or of KAKAKAKAKAKAKAKA (SEQ ID NO: 71 and ADA- DADADADADADAD (SEQ ID NO: 73) would be expected to form membranes, but not any of these peptides alone due to lack of complementarity.

The compositions described herein (regardless of the precise form (e.g., whether in a liquid form or molded) and regardless of the overall compositions (e.g., whether combined with another agent, contained within a device, or packaged in a kit) can include a mixture of RADA16-I (SEQ ID NO: 1) or RADA12-I (SEQ ID NO: 31) and EAKA16-I (SEQ ID NO: 6) or EAK16-II (SEQ ID NO: 18). Other mixtures can include RADA16-II (SEQ ID NO: 4) or RADA12-II and EAKA16-I (SEQ ID NO: 6) or EAKA16-II (SEQ ID NO: 18). Other mixtures can include various lengths of the same peptide sequence or mixtures of modulus I and modulus II peptides. For example, one could use a mixture of RADA12-I (SEQ ID NO: 31) and RADA12-II; of RADA16-I (SEQ ID NO: 1) and RADA16-II (SEQ ID NO: 4); of RADA12-I (SEQ ID NO: 31) and RADA16-I (SEQ ID NO: 1); of RADA12-II and RADA16-II (SEQ ID NO: 4); of EAKA12-I and EAKA12-II; of EAKA16-I (SEQ ID NO: 6) and EAKA 16-II (SEQ ID NO: 18); of EAKA12-I and EAKA16-II (SEQ ID NO: 18); or of EAKA12-II and EAKA16-II (SEQ ID NO: 18). Use of a mixture rather than a single peptide can modulate properties such as the speed of assembly and the stiffness of the assembled material.

In summary, peptides useful in the manner described herein can have, or can include, a sequence of alternating hydrophobic and hydrophilic amino acid residues that are complementary and structurally compatible. As noted, the peptides can vary in length and can be a multiple of four residues, but does not have to be. For example, the peptides can be at least eight amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. The amino acid residues can be selected from D-amino acids or L-amino acids, and the peptides or mixtures of peptides can include combinations thereof. Suitable, naturally-occurring hydrophobic amino acid residues include Ala, Val, Ile, Met, Phe, Tyr, Trp, Ser, Thr and Gly. The hydrophilic amino acid residues can be basic amino acids (e.g., Lys, Arg, His, Orn); acidic amino acids (e.g., Glu, Asp); or amino acids that form hydrogen bonds (e.g., Asn, Gln). If L-amino acids are present in the structure, degradation produces amino acids that may be reused by the host tissue. The fact that L-configured amino acid residues occur naturally within the body distinguishes this class of compounds from numerous other biocompatible substances and may offer unique advantages.

Either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group ($NH_2$) can be used to neutralize an "extra" negative charge that may otherwise be present at the C-terminus (e.g., a charge not resulting from the side chain of the C-terminal amino acid residue). Where an amine is used, the C-terminus would bear an amide (—$CONH_2$). The neutralization of charges on a terminus may facilitate self-assembly. One of ordinary skill in the art will be able to select other suitable groups.

Structures for use in the invention can be formed that have varying degrees of stiffness or elasticity. The structures typically have a low elastic modulus (e.g., a modulus in the range of 1-10 kPa as measured by standard methods, such as in a standard cone-plate rheometer). Low values may be preferable, as they permit structure deformation as a result of movement, in response to pressure, in the event of cell contraction. The desired stiffness of the composition can be dictated by the cell/tissue/organ/tumor to which the composition is to be applied. The stiffness can be controlled in a variety of ways, including by changing the length, sequence, and/or concentration of the precursor molecules (e.g., self-assembling peptides).

Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are within the scope of the present invention. For example, amino acid residues with aromatic rings may be incorporated and cross-linked by exposure to UV light. The extent of cross-linking can be precisely controlled by applying the radiation for a predetermined length of time to peptides of known sequence and concentration. The extent of cross-linking can be determined by light scattering, gel filtration, or scanning electron microscopy using standard methods. Furthermore, cross-linking can be examined by HPLC or mass spectrometry analysis of the structure after digestion with a protease, such as matrix metalloproteases. Material strength may be determined before and after cross-linking. Regardless of whether cross-linking is achieved by a chemical agent or light energy, the molecules may be cross-linked in the course of creating a mold or when self-assembling peptide-containing solutions are applied to the body or tumors of subjects.

The half-life (e.g., the in vivo half-life) of the structures can also be modulated by incorporating protease or peptidase cleavage sites into the precursors that subsequently form a given structure. Proteases or peptidases that occur naturally in vivo, or that are introduced (e.g., by a surgeon), can then promote degradation by cleaving their cognate substrates. Combinations of any of the modifications described here can be made. For example, self-assembling peptides that include a protease cleavage site and a cysteine residue and/or a cross-linking agent, kits and devices containing them, and methods of using them can be utilized.

The peptide structures formed from any self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

Prior to self-assembly the peptides may be contained in (e.g., dissolved in) a solution that is substantially free of ions (e.g., monovalent ions) or that contains a sufficiently low concentration of ions to prevent significant self-assembly (e.g., a concentration of ions less than 10, 5, 1, or 0.1 mM). Self-assembly may be initiated or enhanced at any subsequent time by the addition of an ionic solute or diluent to a peptide solution or by a change in pH. For example, NaCl at a concentration of between approximately 5 mM and 5 M will induce the assembly of macroscopic structures within a short period of time (e.g., within a few minutes). Lower concentrations of NaCl may also induce assembly but at a slower rate. Alternatively, self-assembly may be initiated or enhanced by introducing the peptides (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure) comprising such ions. Generally, self-assembly is, expected to occur upon contacting the peptides with such a solution in any manner.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$, and the concentration of such ions required to induce or enhance self-assembly is typically at least 5 mM (e.g., at least 10, 20, or 50 mM). Lower concentrations also facilitate assembly, though at a reduced rate. When desired, self-assembling peptides can be delivered with a hydrophobic material (e.g. a pharmaceutically acceptable oil) in a concentration that permits self-assembly, but at a reduced rate. When self-assembling peptides are mixed with a hydrophobic agent, such as an oil or lipid, the assembly of the material forms different structures. The structures will appear like ice on a layer of oil but in some cases when another material is added, the material will assemble into various other three dimensional structures that may be suitable for drug loading or other relevant therapeutic agents. The hydrophilic part of the molecule will assemble in such a way to minimize hydrophobic-hydrophilic interaction, thereby creating a barrier between the two environments. Several experiments have shown that the self-assembling peptides will align on the surface of the oil like ice on water with the hydrophobic part of the molecule toward the surface and the hydrophilic portion of the molecule facing away from the oil, or will form toroidal like structures with the hydrophobic material contained inside. This type of behavior enables the encapsulation of therapeutics or other molecule of interested for delivery in the body.

Depending on the formulation and desired properties of the macroscopic structure (e.g., the stiffness of the nanomaterial or the rate of its formation), the concentration of precursors (e.g., self-assembling peptides) can vary from approximately 0.01% w/v (0.1 mg/ml) to approximately 99.99% w/v (999.9 mg/ml), inclusive. For example, the concentration prior to self-assembly can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). In some embodiments, the concentration can also be less than 0.1%. The precursors (e.g., self-assembling peptides) can be formulated as powders and administered in a powder form or resuspended. If dry, the peptides can then self-assemble following contact with bodily fluids (e.g., at the site of the tumor or cancer cell).

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance or cells (e.g. cancer stem cells) in a subject in need thereof. Self-assembly can also be achieved ex vivo by exposure to conditions within a certain range of physiological values (e.g., conditions appropriate for cell or tissue culture). While liquid formulations are readily dispensed, the compositions administered may also be in a gel form that may become stiffer upon contact with the subject's body or tumor.

In one embodiment, the concentration of the self-assembling peptides in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling peptides can be higher in stock solutions and in solid (e.g., powdered) formulations. In solid preparations, the concentration of self-assembling peptides can approach 100% (e.g., the concentration of self-assembling peptides can be 95, 96, 97, 98, 99% or more (e.g., 99.99%) of the composition). Whether in liquid or solid form, the peptides can be brought to the desired concentration prior to use by addition of a diluent (e.g., deionized water), powder, wetting agent, or a therapeutic, diagnostic or prophylactic agent.

Regardless of the precise nature of the self-assembling agents, upon exposure to conditions such as those described herein, the agents can form membranous two- or three-dimensional structures including a stable macroscopic porous matrix having ordered interwoven nanofibers (e.g., fibers approximately 10-20 nm in diameter, with a pore size of about 50-100 nm in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling peptides can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling agents (e.g., peptides) therein. The sequences, characteristics, and properties of the peptides and the structures formed by them upon self-assembly are discussed further below.

The compositions can be formulated as concentrated stocks or in dry form, and these can be diluted or dissolved to form compositions (e.g., biocompatible compositions), which are substantially non-toxic to biological cells in vitro or in vivo. For example, the compositions can contain materials in quantities that do not elicit a significant deleterious effect on the recipient's body (e.g., a prohibitively severe immunological or inflammatory reaction, or unacceptable scar tissue formation).

When a solution containing non-assembled peptides is laid down on a biological tissue or cell (e.g. cancer cell or tumor), the peptides having sufficient proximity to the tissue or cell assemble, causing the solution to gel. Any solution that remains distant from the tissue or cell remains liquid, as the self-assembling peptides have not yet been exposed to conditions that promote their assembly. As the material is disturbed (e.g., by performing a surgical procedure), liquid material appears to gel as it comes into sufficient contact with the body. At times, the compositions can take on characteristics ranging from a liquid to those of a solid, appearing gel- or salve-like or as a slurry).

The term "pharmaceutical excipient," as used herein in the specification and claims, comprises a material such as an adjuvant, a carrier, pH-adjusting and buffering agents, toxicity adjusting agents, wetting agents, preservatives, and the like.

The term "pharmaceutically acceptable," as used herein in the specification and claims, refers to a non-toxic, inert, and/or composition that is physiologically compatible with humans or other mammals.

The term "stasis," as used herein in the specification and claims, refers to a state wherein a cell no longer divides but retains the ability to do so at a later time. The self-renewing ability of cancer stem cells may also be halted while retaining the ability to do so at a later time. The reaction of a cell in stasis mimics the reaction of a cell during cell-cell or cell-extra-cellular matrix interactions.

The term "surgical procedure" or "surgical treatment," as used herein in the specification and claims, refers to procedures performed on a subject in need thereof. The surgical procedure or treatment can involve excision of cells, a tissue, an organ or a tumor. The excised material can be diseased (e.g. cancer burdened) or non-diseased. Surgical procedure or treatment can also involve biopsies to collect a sample from a targeted area. The procedure or treatment can also result in no excision of material.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties of those components. The materials may self-assemble and be transformed in configuration, possibly in combination with other materials, such as body fluids, tissues, or tumors, resulting in inhibition of movement of the fluids, tissues, or tumors. In other aspects, the materials may self-assemble and provide a marking for visualization of boundaries or margins of cells, tissues, organs, or tumors. Some aspects of the invention are described in connection with "self-assembling" or "self-assembled" materials, and it is to be understood that wherever this terminology is used, the materials referred to may, but need not, self-assemble in order to function per the invention. Reference is made to "assembling" materials in some instances, and this is meant to encompass materials that self-assemble and/or undergo another transformation toward use in accordance with the invention. In some cases, a particular material can self-assemble in some environments, and in other environments may not self-assemble at all.

The term "treating" or "treatment" of a disease (e.g. cancer) or "therapeutic," as used herein in the specification and claims, includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease); full eradication of disease is not required.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

The isolation of cells with stem-like properties from prostate tumors suggests the presence of a cancer stem cell (CSC) population, which may account for the initiation, progression, and metastasis as well as drug resistance of the disease. We hypothesized that containing, or at least immobilizing, the CSCs in a nano self-assembling material might help prevent prostate tumor progression or metastasis. Here we report that CSCs from prostate cancer cell lines remained quiescent for more than 28 days when embedded in SAP. When the prostate CSCs were embedded in 1% and 3% SAP, most of the CSCs remained single cells 14 days after plating in a non-adherent plate; no prostaspheres could be detected 14 days after plating, suggesting that self-renewal was significantly suppressed. In the controls, prostate CSCs began to divide one day after plating in a non-adherent plate and prostaspheres were visible at day 10, indicating the active self-renewal property of the prostate CSCs. Our findings suggest that SAP can completely inhibit a prostate CSC from self-renewal while preserving its viability and CSC property. Therefore, SAP can be an effective nanomaterial for inhibiting cancer progression and metastasis to stop the progression during treatment and removal.

Cancer Stem Cells

In one embodiment, the present invention provides a method for inhibiting cancer stem cell division by contacting the exterior of the cancer stem cell with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the exterior of cancer stem cells. It will be understood by those skilled in the art, other similar self-assembling peptides can be used interchangeably with this invention.

Possible cancer stem cells of this embodiment of the invention can include those originating from cancers of the brain, breast, colon, ovary, pancreas, prostate, and blood (i.e. leukemic). In one aspect of the present invention, prostate cancer stem cells are contacted by a nanomaterial (i.e. self-assembling peptide). As would be understood by those skilled in the art, other cancer stem cells can be similarly, or identically, affected by the methods and compositions of the present invention.

In one aspect of the invention, a therapeutically effective amount of the nanomaterial (e.g. self-assembling peptide) can be introduced into a subject to inhibit cancer stem cell division. In another aspect, a pharmaceutically acceptable excipient is introduced in combination with the nanomaterial.

In another embodiment, the present invention provides a method for isolating a cancer cell by contacting the exterior of the cancer cell with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one aspect of the present invention, the self-assembling peptide, RADA16-I, is used to contact the exterior of cancer cells. It will be understood by those skilled in the art, other similar self-assembling peptides can be used interchangeably with this invention.

In another embodiment, the present invention provides a method for inhibiting cancer stem cell colony formation by contacting the exterior of the cancer stem cell with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the exterior of cancer stem cells. It will be understood by those skilled in the art, other similar self-assembling peptides can be used interchangeably with this invention.

Possible cancer stem cells of this embodiment of the invention can include those originating from cancers of the brain, breast, colon, ovary, pancreas, prostate, and blood (i.e. leukemic). In one aspect of the present invention, prostate cancer stem cells are contacted by a nanomaterial (i.e. self-assembling peptide). As will be understood by those skilled in the art, other cancer stem cells can be similarly, or identically, affected by the methods and compositions of the present invention.

In another embodiment, the present invention provides a method for inhibition of self-renewal by contacting the exterior of the cancer stem cell with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the exterior of cancer stem cells. It will be understood by those skilled in the art, other similar self-assembling peptides can be used interchangeably with this invention.

Possible cancer stem cells of this embodiment of the invention can include those originating from cancers of the brain, breast, colon, ovary, pancreas, prostate, and blood (i.e. leukemic). In one aspect of the present invention, prostate cancer stem cells are contacted by a nanomaterial (i.e. self-assembling peptide). As will be understood by those skilled in the art, other cancer stem cells can be similarly, or identically, affected by the methods and compositions of the present invention.

In another embodiment, the present invention provides a method for inhibiting cancer stem cell spheroid formation by contacting the exterior of the cancer stem cell with at least one nanomaterial.

The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the exterior of cancer stem cells. It will be understood by those skilled in the art, other similar self-assembling peptides can be used interchangeably with this invention.

Possible cancer stem cells of this embodiment of the invention can include those originating from cancers of the brain, breast, colon, ovary, pancreas, prostate, and blood (i.e. leukemic). In one aspect of the present invention, prostate cancer stem cells are contacted by a nanomaterial (i.e. self-assembling peptide). As will be understood by those skilled in the art, other cancer stem cells can be similarly, or identically, affected by the methods and compositions of the present invention.

Metastasis of Cancer Cells

In another embodiment, the present invention provides a method for inhibiting metastasis of a cancer cell, the method comprising introducing a nanomaterial to the exterior of the cancer cell. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the exterior of cancer cells. It will be understood by those skilled in the art, other similar self-assembling peptides can be used interchangeably with this invention.

Possible cancer cells of this embodiment of the invention can include those originating from cancers of the brain, lung, connective tissue, mesenchyme, germ cells, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). In one aspect of the present invention, prostate cancer stem cells are contacted by a nanomaterial (i.e. self-assembling peptide). As will be understood by those skilled in the art, other cancer stem cells can be similarly, or identically, affected by the methods and compositions of the present invention. In another aspect of the present invention, the cancer cells can include cancer stem cells. It will be understood by those skilled in the art that the present invention can be applied to other cell types besides cancer cells, notably non-cancerous cell types.

In one aspect of the invention, a therapeutically effective amount of the nanomaterial (e.g. self-assembling peptide) can be introduced into a subject to inhibit metastasis. In another aspect, a pharmaceutically acceptable excipient is introduced in combination with the nanomaterial.

In another embodiment, the present invention provides a method for inhibiting progression of a tumor, the method comprising contacting the tumor with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the tumor. It will be understood by those skilled in the art, other similar self-assembling peptides can be used interchangeably with this invention.

Tumors of this embodiment of the present invention include malignant and non-malignant tumor types. The methods of the invention can be carried out prior to a non-malignant tumor becoming malignant. Possible tumor types to be contacted by the method of this embodiment can include those originating from cells of the brain, lung, connective tissue, mesenchyme, germline, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). In one aspect of the present invention, prostate tumors are contacted by a nanomaterial (i.e. self-assembling peptide). As would be understood by those skilled in the art, other tumor types can be similarly, or identically, affected by the methods and compositions of the present invention.

In one aspect of the invention, a therapeutically effective amount of the nanomaterial (e.g. self-assembling peptide) can be introduced into a subject to inhibit progression of a tumor. In another aspect, a pharmaceutically acceptable excipient is introduced in combination with the nanomaterial.

Treatment of Cancer

In another embodiment, the present invention provides a method for treatment of cancer, the method comprising introducing at least one nanomaterial at the cancer. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the cancer. It will be understood by those skilled in the art, other similar self-assembling peptides can be used interchangeably with this invention.

Cancers that can be treated by the methods of the present invention include carcinoma, sarcoma, leukemia, lymphoma, and central nervous system cancers. In one aspect of the present invention, prostate cancer is treated. As would be understood by those skilled in the art, other cancer types can be similarly, or identically, affected by the methods and compositions of the present invention.

In one aspect of the present invention, one or more chemotherapeutic agents and/or other antitumor agents can also be introduced at the cancer.

In one aspect of the present invention, the cancer can be further treated with radiation. The radiation can include ionizing radiation. The ionizing radiation can include x-rays, gamma rays, or particle radiation. Particle radiation can include electrons, protons, neutrons, alpha particles, and beta particles.

In one aspect of the present invention, the cancer can be further treated by freezing. The source would typically be liquid nitrogen or argon gas.

In one aspect of the present invention, the cancer can be treated with one or more nanomaterial and one or more chemotherapeutic agent. In another aspect of the present invention, the cancer can be treated with one or more nanomaterial and radiation. In another aspect of the present invention, the cancer can be treated with one or more nanomaterial and freezing. In another aspect of the present invention, the cancer can be treated with one or more nanomaterial and any combination of the following: freezing, one or more chemotherapeutic agent, and radiation. In yet another aspect of the present invention, the cancer can be treated with one or more self-assembling peptide and any combination of the following: freezing, one or more chemotherapeutic agent, and radiation.

In one aspect of the invention, a therapeutically effective amount of the nanomaterial (e.g. self-assembling peptide) can be introduced into a subject to treat cancer. In another aspect, a pharmaceutically acceptable excipient can be introduced in combination with the nanomaterial.

Induction and Maintenance of Cell Stasis

In another embodiment, the present invention provides a method for inducing cell stasis, the method comprising contacting the exterior of the at least one cell with at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the cell. It will be understood by those skilled in the art, other similar self-assembling peptides can be used interchangeably with this invention.

In another aspect of the present invention, cells from a vertebrate animal can be used. Possible cells useful in this embodiment of the invention can include those originating from the brain, lung, connective tissue, mesenchyme, germ cells, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). As would be understood by those skilled in the art, other cell types can be similarly, or identically, affected by the methods and compositions of the present invention. In another aspect of the present invention, the cells can include cancer cells. In another aspect of the present invention, the cells can include cancer stem cells. In another aspect of the present invention, the cells from an invertebrate can be used. It would be understood by those skilled in the art that the present invention can be applied to virtually any cell type.

In another embodiment, the present invention provides a method for inducing and maintaining stasis in cultured cells, the method comprising: seeding at least one cell in a vessel and contacting the at least one cell with at least one nanomaterial, whereby the at least one nanomaterial self-assembles around the at least one cell, causing stasis. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is used to contact the cell. It will be understood by those skilled in the art, other similar self-assembling peptides can be used interchangeably with this invention.

In another aspect of the present invention, cells from a vertebrate animal can be used. Possible cells of this embodiment of the invention can include those originating from the brain, lung, connective tissue, mesenchyme, germ cells, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). As would be understood by those skilled in the art, other cell types can be similarly, or identically, affected by the methods and compositions of the present invention. In another aspect of the present invention, the cells can include cancer cells. In another aspect of the present invention, the cells can include cancer stem cells. In another aspect of the present invention, the cells from an invertebrate can be used. It would be understood by those skilled in the art that the present invention can be applied to virtually any cell type.

A vessel for seeding cells can include any cell culture vessel made of plastic, glass, or other composite materials used by those skilled in the art.

Compositions, Cell Culture, and Kits

In another embodiment, the present invention provides a composition that inhibits cancer cell division, the composition comprising at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide of the composition is RADA16-I. It will be understood by those skilled in the art, other similar self-assembling peptides could be used interchangeably with this invention.

In one aspect of the present invention, the composition can include one or more chemotherapeutic agents and/or other antitumor agents.

In one aspect of the invention, a therapeutically effective amount of the composition can be used to inhibit cancer cell division. In another aspect, a pharmaceutically acceptable excipient can be introduced in combination with the composition.

In another embodiment, the present invention provides a composition for coating a tumor, the composition comprising at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide of the composition is RADA16-I. It will be understood by those skilled in the art, other similar self-assembling peptides could be used interchangeably with this invention.

In one aspect of the present invention, the composition can include one or more chemotherapeutic agents and/or other antitumor agents.

In another embodiment, the present invention provides a method for treatment of cancer by introducing a composition that inhibits cancer cell division, the composition comprising at least one nanomaterial. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is included in the composition. It will be understood by those skilled in the art, other similar self-assembling peptides could be used interchangeably with this invention.

Possible cancer types that can be treated by this embodiment of the invention can include those originating from cancers of the brain, lung, connective tissue, mesenchyme, germ cells, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). In one aspect of the present invention, prostate cancer can be treated by the composition. As would be understood by those skilled in the art, other cancer types can be similarly, or identically, affected by the methods and compositions of the present invention. It would be understood by those skilled in the art that the present invention can be applied to non-cancerous cell types as well.

In one aspect of the invention, a therapeutically effective amount of the composition can be introduced into a subject. The introduction of the composition can be at the site of the cancer. The introduction of the composition can also occur adjacent to the cancer. Also, the introduction of the composition into the subject can occur in some other region of the body away from the cancer. In another aspect, a pharmaceutically acceptable excipient can be introduced in combination with the nanomaterial.

In one aspect of the present invention, the composition being introduced to the cancer can include one or more chemotherapeutic agents and/or other antitumor agents.

In one aspect of the present invention, the cancer can be treated with the composition of the present invention and one or more chemotherapeutic agent. In another aspect of the present invention, the cancer can be treated with the composition of the present invention and radiation.

In another aspect of the present invention, the cancer can be treated with the composition of the present invention and freezing. In another aspect of the present invention, the cancer can be treated with the composition of the present invention and any combination of the following: freezing, one or more chemotherapeutic agent, and radiation.

In another embodiment, the present invention provides a cell culture comprising at least one cell and a nanomaterial, wherein the nanomaterial assembles around the at least one cell.

The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is included in the composition. It will be understood by those skilled in the art, other similar self-assembling peptides could be used interchangeably with this invention.

In another aspect of the present invention, cells from a vertebrate animal can be used. Possible cells of this embodiment of the invention can include those originating from the brain, lung, connective tissue, mesenchyme, germ cells, testes, eyes, skin, kidney, lymphatics, adrenal gland, cervix, esophagus, stomach, head and neck, liver, larynx, neurons, urethra, vagina, bladder, bone, breast, colon, ovary, pancreas, prostate, and blood (i.e. leukemic). As would be understood by those skilled in the art, other cell types can be similarly, or identically, affected by the methods and compositions of the present invention. In another aspect of the present invention, the cells can include cancer cells. In another aspect of the present invention, the cells can include cancer stem cells. In another aspect of the present invention, the cells from an invertebrate can be used. It would be understood by those skilled in the art that the present invention can be applied to virtually any cell type.

In another embodiment, the present invention provides a kit for inhibiting cancer progression, the kit comprising at least one nanomaterial solution and at least one chemotherapeutic agent. The kit also includes instructions for use of the kit. The nanomaterial solution is made up of a nanomaterial dissolved or suspended in water or any type of buffer solution known to those skilled in the art. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, is included in the nanomaterial solution. It will be understood by those skilled in the art, other similar self-assembling peptides could be used interchangeably with this invention.

Surgical Applications

In another embodiment, the present invention provides a method for inhibiting metastasis of cancer cells before, during, or after a surgical treatment or procedure, the method comprising: introducing at least one nanomaterial at the area of surgical procedure and performing the surgical procedure, whereby the at least one nanomaterial surrounds the cancer cells and inhibits release of the cancer cells into the area of surgical procedure, thus inhibiting metastasis. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, can be used in the method. It will be understood by those skilled in the art, other similar self-assembling peptides could be used interchangeably with this invention.

In one aspect of the present invention, the surgical procedure is a biopsy. A biopsy can include an aspiration (fine needle), a cone biopsy, a core needle biopsy, a suction assisted core biopsy, an endoscopic biopsy, a punch biopsy, a surface biopsy, or an excisional (surgical) biopsy. In one aspect, fine needle biopsy is performed as the surgical procedure. In another aspect, excision of either a piece or the entire tumor or cancer cell is performed.

In one aspect of the invention, a therapeutically effective amount of the nanomaterial (e.g. self-assembling peptide) can be introduced into a subject to inhibit metastasis. In another aspect, a pharmaceutically acceptable excipient can be introduced in combination with the nanomaterial.

In another embodiment, the present invention provides a method for inhibiting bleeding during and after a surgical treatment or procedure, the method comprising introducing at least one nanomaterial at an area of surgical procedure. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, can be used in the method. It will be understood by those skilled in the art, other similar self-assembling peptides could be used interchangeably with this invention.

In one aspect of the invention, a therapeutically effective amount of the nanomaterial (e.g. self-assembling peptide) can be introduced into a subject to inhibit movement of cells. In another aspect, a pharmaceutically acceptable excipient can be introduced in combination with the nanomaterial.

In one aspect of the invention, the nanomaterial can be introduced in combination with a blood coagulation factor or other mechanical means, such as stitches. The nanomaterial can also be introduced before or after the blood coagulation factor, or other mechanical means, is introduced.

In one aspect of the present invention, the surgical procedure is a biopsy. A biopsy can include an aspiration (fine needle), a cone biopsy, a core needle biopsy, a suction assisted core biopsy, an endoscopic biopsy, a punch biopsy, a surface biopsy, or an excisional (surgical) biopsy. In one aspect, fine needle biopsy is performed as the surgical procedure. In another aspect, excision of a piece, or the entire tumor, cancer cell, or tissue, is performed. It would be understood by those skilled in the art that the invention could be applied to virtually any surgical procedure or treatment, including those procedures that involve diseased and non-diseased organs, tissues, and cells.

In another embodiment, the present invention provides a method for marking the margins of a tumor, the method comprising introducing at least one nanomaterial at the tumor, whereby the at least one nanomaterial self-assembles around the margins of the tumor, providing the marking. The nanomaterial can be a plurality of self-assembling peptides. The self-assembling peptides can include any of a number of self-assembling peptides known to those skilled in the art. Self-assembling peptides of this invention can include amphiphilic peptides that comprise substantially equal proportions of hydrophobic and hydrophilic amino acids and are complementary and structurally compatible. In one exemplary aspect of the present invention, the self-assembling peptide, RADA16-I, can be used in the method. It will be understood by those skilled in the art, other similar self-assembling peptides could be used interchangeably with this invention.

In one aspect of the invention, the nanomaterial is linked to a molecular tag, or label, to aid in visualization of the margins.

EXAMPLES

The following examples are included to demonstrate certain embodiments of the invention. It should be appreciated by those of skill in the art that the techniques disclosed in the examples represent techniques that function well in the practice of the invention. However, those of skill in the art should, in light of the present disclosure, appreciate that many changes can be made in the specific embodiments which are disclosed and still obtain a similar result without departing from the scope of the invention.

Preparation of the Sap Solution

The SAP solution was prepared by using RADA16-I dry powder (made in the Ellis-Behnke lab) and mixed in an Eppendorf tube. The solution contained 10 or 30 mg of RADA16-I powder in 1 ml of Milli-Q water (Millipore Corp., Billerica Mass.), mixed, then sonicated for 30 seconds and filtered; this produced 1% and 3% SAP, respectively.

Culture Medium Preparation

Pre-mix medium for spheroid assay. Mix 50 ml SFM (DMEM-F12-high glucose with 0.25% methylcellulose) and add 1 ml b27 per 50 ml SFM (50× stock). The growth factors are: fibroblast growth factor-basic (FGF) (Sigma cat. no. F0291)—25 µg dissolved in 1.0 ml of 5 mM Tris (pH 7.6) and sterilized with a 0.22 µm pore size filter (make 20 µl aliquots (stored at −20° C.) and add 10 µl per 50 ml of SFM); Epidermal growth factor (EGF) (Sigma cat. no. E4127)— 0.1 mg dissolved in 1.0 ml of phosphate-buffered saline containing 0.1% bovine serum albumin (Sigma cat. no. A7511) (make 20 ml aliquots (stored at −20° C.) and add 10 µl per 50 ml of SFM); Insulin 10 mg/ml—add 20 µl per 50 ml.

Cell Preparation

To remove prostate cancer cells (DU145, ATCC, Rockville, Md.) from adherent culture, trypsin was used to liberate and then re-suspend 400 cells per 1 µl plated in each well (10). Before plating the cells, the plate was coated with polyhema (Sigma, St. Louis, Mo.).

SAP Preparation

Untreated SAP solution has a very low pH (about 3-4). We neutralized the SAP solution in culture medium before implanting cells in the material. Briefly, for both 1% and 3%, SAP was placed in a dry dish and then 500 µl of culture medium added at the edge of the dish. This was to ensure that the culture medium would not wash the SAP away. The self-assembly occurred as soon as the material made contact with the medium. The medium was changed once at 30 minutes, and then removed. The 400 cells were placed either in the assembled SAP or a control well. Culture medium was then added at the edge of the dish in both SAP cases, and topped up every 2 days to compensate for evaporation. On day 14, the cells were vigorously washed out of the SAP using culture medium. In the 1% case, group 1 (n=4), the cells and SAP were moved to a new well and contents were washed multiple times to separate them from the SAP. In the 3% case, group 2 (n=4), the wells were also vigorously washed to remove the cells from the SAP. However, in both the 1% and 3% SAP concentration, not all of the cells were liberated. The culture continued to grow for 28 days at which point the wells were fixed with 4% paraformaldahyde.

Imaging of Cultures

The cultures were observed with an inverted microscope and pictures were taken.

1% SAP Concentration

In group 1 (n=4), the cells in the 1% SAP remained quiescent (FIGS. 1A, D, G and J). When the cells were washed out of the material, the colony formation proceeded in a normal fashion. After replating the washed out 1% SAP group of cells into the non-adherent plate, prostaspheres were visible after 8 days (FIG. 1M), with colonization visible beginning at 10 days post-washout, confirming that CSC-embedded cells were viable and capable of self-renewal. However, the remaining cells in each of the four wells of the 1% SAP continued to be quiescent for up to 28 days, showing no evidence of division and colony formation. In the majority of cells that were washed free of the 1% material, colony formation proceeded (FIG. 1M).

3% SAP Concentration

Group 2 (n=4) results were similar to group 1. In the 3% SAP, no colony formed while cells were resident in the material (FIGS. 1B, E, H, K and L). When the cells were washed free of the material, the percentage of cells that were retained by the SAP was much greater in the 3% material than in the 1%. The cells that remained in the material showed no cell division or colony formation at 28 days. In the cells that were washed out of the SAP, prostaspheres were evident in 8 days post-washout and colony formation proceeded, similar in size and growth rate as the controls (FIG. 1N). FIG. 1O shows a colony that was formed when the cell was washed out of the 3% material. Next to the colony there is a cell that is still encased in the material and has not divided (FIG. 1O, inset).

Controls

In the controls (n=2), the colony formation began as early as day 1 (FIG. 1C) and proceeded such that at the end of 10 days all of the cells that were floating had formed colonies (FIG. 1I). The colony size was similar in the experimental groups at the end of 28 days for all of the floating cells.

Results

Metastatic prostate cancer cells (DU145), when placed in 1% concentration SAP (group 1) and 3% concentration SAP (group 2), saw delayed division and formation of colonies for the duration of the cells' encapsulation in the material. In the controls, all of the cells that were floating had formed colonies by the end of 14 days. However, if the cells were completely surrounded by the material, no colonies were seen. In some cases, if part of the cell was exposed, a colony of reduced size was seen. We were able to suspend the proliferation of cells out to 28 days; then the experiment was stopped.

Discussion

The use of the nanomaterial stops the formation of colonies in cancer stem cells, appearing to mimic extracellular matrix (ECM) and cell-cell contact. Unlike Matrigel™, the material does not contain any other additives; the only difference between the groups was the concentration of the material.

Cell Division is Stopped

In each group, cells placed in the SAP stopped both the division of cancer cells in vitro and subsequent colony formation. This shows that colonization of stem cells could be delayed in order to stop or slow the metastasis of cancer cells before or during a surgical procedure or treatment.

Cells Remain Alive and in Stasis

The nanomaterials appear to mimic cell-cell interaction, thus causing the cell to go into stasis, stop dividing and inhibit tumor progression and metastasis by suppressing the self-renewing ability of the prostate CSCs.

Stasis does not Change the Phenotype of the Cell

Once the cells are liberated from the material, they will grow and multiply, similar to the control cells when first placed into the culture medium.

Cancer Stem Cells Unaltered

The ability to form spheroids under non-adherent culture condition is one of the characteristics of cancer stem cells. Cells that are liberated from the nanomaterial not only can proliferate, but can also form spheroids again in floating culture, demonstrating that the stem cell property of the prostate cancer cells was preserved by the self-assembled nanomaterials.

CONCLUSIONS

One area that has been a problem for cancer spread is malignant seeding. The term is often used in the context of the inadvertent spread of cancer cells through clinical processes (5) (2) (8). Tumors that are biopsied, or otherwise 'interfered with,' have a higher incidence of metastasis than tumors that were removed in an untouched block with wide margins and good tumor hygiene. The nanomaterials of the present invention could be used to stop the spread and limit the growth of metastatic cells by tricking them into thinking they are next to other cancer cells. This slows or stops the signal that triggers the spread of cancer cells. Likewise, if a channel is created by the nanomaterial for needle insertion and removal in tumors, cells will be stripped from the needle at the interface of the tumor and the nanomaterial; thus, inhibition of the escape of cancer cells along the biopsy track is accomplished.

The use of the nanomaterial of the present invention allows us to mimic the ECM of the tumor environment, tricking metastasis, thus slowing the tumor growth and allowing for a more thorough and effective treatment.

An in vitro embodiment of the present invention can include a system to study the spread and/or interaction of cancer cells in three dimensions, wherein by changing the sequence, it is possible to observe various interactions and study transformation of cancer cells and the contribution of the physical and/or chemical environment. This is possible since the environment created by the nanomaterial mimics the ECM of early development and how it changes over time.

By injecting the nanomaterial directly into the tumor one can inhibit stop the spread of metastatic cells before or during resection. In addition, by loading the SAP material with chemotherapeutic agents, the efficacy of the localized treatment can be increased due to the increased contact time.

REFERENCES

1. Chaudhary, P. M.; Roninson, I. B. Expression and activity of P-glycoprotein, a multidrug efflux pump, in human hematopoietic stem cells. Cell 66(1):85-94; 1991.2.
2. Diaz, L. K.; Wiley, E. L.; Venta, L. A. Are malignant cells displaced by large-gauge needle core biopsy of the breast? AJR Am J Roentgenol 173(5):1303-1313; 1999.
3. Ellis-Behnke, R. G.; Liang, Y. X.; Guo, J.; Tay, D. K. C.; Schneider, G. E.; Teather, L. A.; Wu, W.; So, K. F. Forever young: how to control the elongation, differentiation and proliferation of cells using nanotechnology. Cell Transplant., in press.
4. Ellis-Behnke, R. G.; Liang, Y. X.; You, S. W.; Tay, D. K.; Zhang, S.; So, K. F.; Schneider, G. E. Nano neuro knitting: peptide nanofiber scaffold for brain repair and axon regeneration with functional return of vision. Proc Natl Acad Sci USA 103(13):5054-5059; 2006.
5. Fortner, J. G. Inadvertent spread of cancer at surgery. J Surg Oncol 53(3):191-196; 1993.
6. Holtz, M.; Forman, S. J.; Bhatia, R. Growth factor stimulation reduces residual quiescent chronic myelogenous leukemia progenitors remaining after imatinib treatment. Cancer Res 67(3):1113-1120; 2007.
7. Hope, K. J.; Jin, L.; Dick, J. E. Acute myeloid leukemia originates from a hierarchy of leukemic stem cell classes that differ in self-renewal capacity. Nat Immunol 5(7): 738-743; 2004.
8. Hu, X. C.; Chow, L. W. Fine needle aspiration may shed breast cells into peripheral blood as determined by RT-PCR. Oncology 59(3):217-222; 2000.
9. Kobayashi, N.; Navarro-Alvarez, N.; Soto-Gutierrez, A.; Kawamoto, H.; Kondo, Y.; Yamatsuji, T.; Shirakawa, Y.; Naomoto, Y.; Tanaka, N. Cancer stem cell research: current situation and problems. Cell Transplant 17(1-2): 19-25; 2008.
10. Ling, M. T.; Wang, X.; Ouyang, X. S.; Xu, K.; Tsao, S. W.; Wong, Y. C. Id-1 expression promotes cell survival through activation of NF-kappaB signalling pathway in prostate cancer cells. Oncogene 22(29):4498-4508; 2003.

11. Maitland, N. J.; Collins, A. T. Prostate cancer stem cells: a new target for therapy. J Clin Oncol 26(17):2862-2870; 2008.
12. Petrylak, D. P.; Tangen, C. M.; Hussain, M. H.; Lara, P. N., Jr.; Jones, J. A.; Taplin, M. E.; Burch, P. A.; Berry, D.; Moinpour, C.; Kohli, M. and others. Docetaxel and estramustine compared with mitoxantrone and prednisone for advanced refractory prostate cancer. N Engl J Med 351 (15):1513-1520; 2004.
13. Reya, T.; Morrison, S. J.; Clarke, M. F.; Weissman, I. L. Stem cells, cancer, and cancer stem cells. Nature 414 (6859):105-111; 2001.
14. Tannock, I. F.; de Wit, R.; Berry, W. R.; Horti, J.; Pluzanska, A.; Chi, K. N.; Oudard, S.; Theodore, C.; James, N. D.; Turesson, I. and others. Docetaxel plus prednisone or mitoxantrone plus prednisone for advanced prostate cancer. N Engl J Med 351(15):1502-1512; 2004.
15. Zhou, S.; Schuetz, J. D.; Bunting, K. D.; Colapietro, A. M.; Sampath, J.; Morris, J. J.; Lagutina, I.; Grosveld, G. C.; Osawa, M.; Nakauchi, H. and others. The ABC transporter Bcrpl/ABCG2 is expressed in a wide variety of stem cells and is a molecular determinant of the side-population phenotype. Nat Med 7(9):1028-1034; 2001.

The above references are herein incorporated by reference in their entirety to the extent they are not inconsistent with the explicit teachings herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for inducing cell stasis, comprising
   (a) contacting the exterior surface of at least one cell with an effective amount of self-assembling peptides to completely surround the cell,
   wherein the self-assembling peptides have a length of 8 to 200 amino acid residues conforming to one or more of Formulas I-IV:

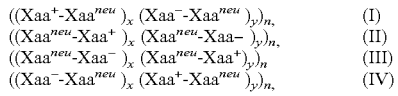

|  |  |
|---|---|
| $((Xaa^+\text{-}Xaa^{neu})_x (Xaa^-\text{-}Xaa^{neu})_y)_n$, | (I) |
| $((Xaa^{neu}\text{-}Xaa^+)_x (Xaa^{neu}\text{-}Xaa^-)_y)_n$, | (II) |
| $((Xaa^{neu}\text{-}Xaa^-)_x (Xaa^{neu}\text{-}Xaa^+)_y)_n$ | (III) |
| $((Xaa^-\text{-}Xaa^{neu})_x (Xaa^+\text{-}Xaa^{neu})_y)_n$, | (IV) | wherein $Xaa^+$ is an amino acid residue having a positive charge; $Xaa^-$ is an amino acid residue having a negative charge; $Xaa^{neu}$ is an amino acid residue having a neutral charge; x and y are integers having a value of 1, 2, or 4, independently; and n is an integer having a value from 1 to 10; and
   wherein the self-assembling peptides are not substantially self-assembled; and
   (b) inducing assembly of the self-assembling peptides, to form a self-assembled structure that encapsulates the cell.

2. The method of claim 1, wherein the cell is a cancer stem cell, wherein division, spheroid formation, or self-renewal of the cancer stem cell is inhibited.

3. The method of claim 1, wherein the self-assembling peptides comprise the amino acid sequence RADARADARADARADA.

4. The method of claim 2, wherein the cancer stem cell is a prostate cancer stem cell.

5. The method of claim 2, wherein inducing stasis inhibits metastasis of the cancer cell.

6. The method of claim 1, wherein self-assembling peptides are in solution at a concentration of between 1% weight to volume and 3% weight to volume.

7. The method of claim 5, wherein the cancer cell is a prostate cancer cell.

8. The method of claim 5, wherein the cancer cell is a cancer stem cell.

9. The method of claim 1, wherein the cell is a vertebrate cancer stem cell.

10. The method of claim 1, wherein the cell is in a tumor.

11. The method of claim 10, wherein the tumor is a prostate tumor.

12. The method of claim 1, wherein the cell is a cancer cell.

13. The method of claim 12, further comprising treating the cancer with radiation or freezing.

14. The method of claim 10, further comprising treating the tumor with radiation or freezing.

15. The method of claim 12, further comprising treating the cancer with radiation.

16. The method of claim 12 performed before, during, or after a surgical procedure, the method further comprising:
   introducing a metastasis-inhibiting effective amount of the self-assembling peptides at the area of surgical procedure; and
   performing the surgical procedure,
   whereby the self-assembling peptides surround the cancer cells and inhibit release of the cancer cells into the area of surgical procedure, thereby inhibiting metastasis.

17. The method of claim 16, wherein the surgical procedure is a biopsy.

18. The method of claim 1, wherein $Xaa^+$ is selected from arginine, lysine, and histidine.

19. The method of claim 1, wherein $Xaa^-$ is selected from aspartic acid and glutamic acid.

20. The method of claim 1, wherein $Xaa^{neu}$ is selected from alanine, valine, leucine, isoleucine, and glycine.

* * * * *

SEQUENCE LISTING

```
<160> NUMBER OF SEQ ID NOS: 76

<210> SEQ ID NO 1
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 2

Arg Ala Asp Ala Arg Gly Asp Ala Arg Ala Asp Ala Arg Gly Asp Ala
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 3

Arg Ala Asp Ala Arg Ala Asp Ala
```

```
1               5

<210> SEQ ID NO 4
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 5

Arg Ala Arg Ala Asp Ala Asp Ala
1               5

<210> SEQ ID NO 6
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 7

Ala Glu Ala Lys Ala Glu Ala Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 9

Arg Ala Glu Ala Arg Ala Glu Ala
1               5
```

```
<210> SEQ ID NO 10
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 10

Lys Ala Asp Ala Lys Ala Asp Ala Lys Ala Asp Ala Lys Ala Asp Ala
 1               5                  10                  15

<210> SEQ ID NO 11
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 11

Lys Ala Asp Ala Lys Ala Asp Ala
 1               5

<210> SEQ ID NO 12
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 12

Ala Glu Ala Glu Ala His Ala His Ala Glu Ala Glu Ala His Ala His
 1               5                  10                  15

<210> SEQ ID NO 13
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 13

Ala Glu Ala Glu Ala His Ala His
 1               5

<210> SEQ ID NO 14
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 14

Phe Glu Phe Glu Phe Lys Phe Lys Phe Glu Phe Glu Phe Lys Phe Lys
 1               5                  10                  15

<210> SEQ ID NO 15
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 15

Phe Glu Phe Lys Phe Glu Phe Lys
 1               5
```

```
<210> SEQ ID NO 16
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 19

Ala Glu Ala Glu Ala Glu Ala Glu Ala Lys Ala Lys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 20

Ala Glu Ala Glu Ala Lys Ala Lys
1               5

<210> SEQ ID NO 21
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 21

Lys Ala Lys Ala Lys Ala Lys Ala Glu Ala Glu Ala Glu Ala Glu Ala
1               5                   10                  15
```

```
<210> SEQ ID NO 22
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 22

Ala Glu Ala Glu Ala Glu Ala Glu Ala Lys Ala Lys Ala Lys Ala Lys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 23

Arg Ala Arg Ala Arg Ala Arg Ala Asp Ala Asp Ala Asp Ala Asp Ala
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 24

Ala Asp Ala Asp Ala Asp Ala Asp Ala Arg Ala Arg Ala Arg Ala Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 25

Asp Ala Asp Ala Asp Ala Asp Ala Arg Ala Arg Ala Arg Ala Arg Ala
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 26

Ala Asp Ala Asp Ala Asp Ala Asp Ala Arg Ala Arg Ala Arg Ala Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 27

His Glu His Glu His Lys His Lys His Glu His Glu His Lys His Lys
1               5                   10                  15

<210> SEQ ID NO 28
```

```
<211> LENGTH: 8
<212> TYPE: PRT
<213> ORGANISM: Artificial Sequence
<220> FEATURE:
<223> OTHER INFORMATION: Exemplary self assembling peptide

<400> SEQUENCE: 28

His Glu His Glu His Lys His Lys
1               5

<210> SEQ ID NO 29
<211> LENGTH: 20
<212> TYPE: PRT
<213> ORGANISM: Artificial Sequence
<220> FEATURE:
<223> OTHER INFORMATION: Exemplary self assembling peptide

<400> SEQUENCE: 29

Val Glu Val Glu Val Glu Val Glu Val Glu Val Glu Val Glu Val Glu
1               5                   10                  15

Val Glu Val Glu
            20

<210> SEQ ID NO 30
<211> LENGTH: 20
<212> TYPE: PRT
<213> ORGANISM: Artificial Sequence
<220> FEATURE:
<223> OTHER INFORMATION: Exemplary self assembling peptide

<400> SEQUENCE: 30

Arg Phe Arg Phe Arg Phe Arg Phe Arg Phe Arg Phe Arg Phe Arg Phe
1               5                   10                  15

Arg Phe Arg Phe
            20

<210> SEQ ID NO 31
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 31

Arg Ala Asp Ala Arg Ala Asp Ala Arg Ala Asp Ala
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 32

Ala Arg Ala Asp Ala Arg Ala Asp Ala Arg Ala Asp
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 33
```

```
Ala Lys Ala Asp Ala Lys Ala Asp Ala Lys Ala Asp
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 34

```
Ala His Ala Asp Ala His Ala Asp Ala His Ala Asp
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 35

```
Ala Arg Ala Glu Ala Arg Ala Glu Ala Arg Ala Glu
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 36

```
Ala Lys Ala Glu Ala Lys Ala Glu Ala Lys Ala Glu
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 37

```
Ala His Ala Glu Ala His Ala Glu Ala His Ala Glu
1               5                   10
```

<210> SEQ ID NO 38
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 38

```
Ala Lys Ala Lys Ala Glu Ala Glu Ala Lys Ala Lys Ala Glu Ala Glu
1               5                   10                  15
```

<210> SEQ ID NO 39
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 39

```
Ala Lys Ala Glu Ala Lys Ala Glu Ala Lys Ala Glu Ala Lys Ala Glu
```

```
<210> SEQ ID NO 40
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 40

Glu Ala Lys Ala Glu Ala Lys Ala Glu Ala Lys Ala Glu Ala Lys Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 41

Lys Ala Glu Ala Lys Ala Glu Ala Lys Ala Glu Ala Lys Ala Glu Ala
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 42

Ala Asp Ala Asp Ala Arg Ala Arg Ala Asp Ala Asp Ala Arg Ala Arg
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 43

Ala Arg Ala Asp Ala Arg Ala Asp Ala Arg Ala Asp Ala Arg Ala Asp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 44

Asp Ala Arg Ala Asp Ala Arg Ala Asp Ala Arg Ala Asp Ala Arg Ala
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 45

Ala Asp Ala Arg Ala Asp Ala Arg Ala Asp Ala Arg Ala Asp Ala Arg
1               5                   10                  15
```

```
<210> SEQ ID NO 46
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 46

Ala Arg Ala Asp Ala Lys Ala Glu Ala Arg Ala Asp Ala Lys Ala Glu
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 47

Ala Lys Ala Glu Ala Arg Ala Asp Ala Lys Ala Glu Ala Arg Ala Asp
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 48

Ala Arg Ala Lys Ala Asp Ala Glu Ala Arg Ala Lys Ala Asp Ala Glu
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 49

Ala Lys Ala Arg Ala Glu Ala Asp Ala Lys Ala Arg Ala Asp Ala Glu
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 50

Ala Gln Ala Gln Ala Gln Ala Gln Ala Gln Ala Gln Ala Gln Ala Gln
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 51

Val Gln Val Gln Val Gln Val Gln Val Gln Val Gln Val Gln Val Gln
1               5                   10                  15
```

```
<210> SEQ ID NO 52
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 52

Tyr Gln Tyr Gln Tyr Gln Tyr Gln Tyr Gln Tyr Gln Tyr Gln Tyr Gln
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 53

His Gln His Gln His Gln His Gln His Gln His Gln His Gln His Gln
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 54

Ala Asn Ala Asn Ala Asn Ala Asn Ala Asn Ala Asn Ala Asn Ala Asn
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 55

Val Asn Val Asn Val Asn Val Asn Val Asn Val Asn Val Asn Val Asn
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 56

Val Asn Tyr Asn Tyr Asn Tyr Asn Tyr Asn Tyr Asn Tyr Asn Tyr Asn
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 57

His Asn His Asn His Asn His Asn His Asn His Asn His Asn His Asn
1               5                   10                  15
```

<210> SEQ ID NO 58
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 58

Ala Asn Ala Gln Ala Asn Ala Gln Ala Asn Ala Gln Ala Asn Ala Gln
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 59

Ala Gln Ala Asn Ala Gln Ala Asn Ala Gln Ala Asn Ala Gln Ala Asn
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 60

Val Asn Val Gln Val Asn Val Gln Val Asn Val Gln Val Asn Val Gln
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 61

Val Gln Val Asn Val Gln Val Asn Val Gln Val Asn Val Gln Val Asn
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 62

Tyr Asn Tyr Gln Tyr Asn Tyr Gln Tyr Asn Tyr Gln Tyr Asn Tyr Gln
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 63

Tyr Gln Tyr Asn Tyr Gln Tyr Asn Tyr Gln Tyr Asn Tyr Gln Tyr Asn
1               5                   10                  15

<210> SEQ ID NO 64

```
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 64

His Asn His Gln His Asn His Gln His Asn His Gln His Asn His Gln
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 65

His Gln His Asn His Gln His Asn His Gln His Asn His Gln His Asn
1               5                   10                  15

<210> SEQ ID NO 66
<211> LENGTH: 18
<212> TYPE: PRT
<213> ORGANISM: Artificial Sequence
<220> FEATURE:
<223> OTHER INFORMATION: Exemplary self assembling peptide

<400> SEQUENCE: 66

Ala Lys Ala Gln Ala Asp Ala Lys Ala Gln Ala Asp Ala Lys Ala Gln
1               5                   10                  15

Ala Asp

<210> SEQ ID NO 67
<211> LENGTH: 18
<212> TYPE: PRT
<213> ORGANISM: Artificial Sequence
<220> FEATURE:
<223> OTHER INFORMATION: Exemplary self assembling peptide

<400> SEQUENCE: 67

Val Lys Val Gln Val Asp Val Lys Val Gln Val Asp Val Lys Val Gln
1               5                   10                  15

Val Asp

<210> SEQ ID NO 68
<211> LENGTH: 18
<212> TYPE: PRT
<213> ORGANISM: Artificial Sequence
<220> FEATURE:
<223> OTHER INFORMATION: Exemplary self assembling peptide

<400> SEQUENCE: 68

Tyr Lys Tyr Gln Tyr Asp Tyr Lys Tyr Gln Tyr Asp Tyr Lys Tyr Gln
1               5                   10                  15

Tyr Asp

<210> SEQ ID NO 69
<211> LENGTH: 18
<212> TYPE: PRT
<213> ORGANISM: Artificial Sequence
<220> FEATURE:
<223> OTHER INFORMATION: Exemplary self assembling peptide

<400> SEQUENCE: 69
```

His Lys His Gln His Asp His Lys His Gln His Asp His Lys His Gln
1               5                   10                  15

His Asp

<210> SEQ ID NO 70
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 70

Ala Asp Ala Asp Ala Lys Ala Lys Ala Asp Ala Asp Ala Lys Ala Lys
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 71

Lys Ala Lys Ala Lys Ala Lys Ala Lys Ala Lys Ala Lys Ala Lys Ala
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 72

Glu Ala Glu Ala Glu Ala Glu Ala Glu Ala Glu Ala Glu Ala Glu Ala
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 73

Ala Asp Ala Asp Ala Asp Ala Asp Ala Asp Ala Asp Ala Asp Ala Asp
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 74

Ala Arg Ala Arg Ala Asp Ala Asp Ala Arg Ala Arg Ala Asp Ala Asp
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Exemplary self assembling peptide

<400> SEQUENCE: 75

```
Val Arg Val Arg Val Asp Val Asp Val Arg Val Arg Val Asp Val Asp
1               5                   10                  15

<210> SEQ ID NO 76
<211> LENGTH: 12
<212> TYPE: PRT
<213> ORGANISM: Artificial Sequence
<220> FEATURE:
<223> OTHER INFORMATION: Exemplary self assembling peptide

<400> SEQUENCE: 76

Arg Ala Arg Ala Arg Ala Asp Ala Asp Ala Asp Ala
1               5                   10
```